(12) United States Patent
Tymianski et al.

(10) Patent No.: US 9,433,685 B2
(45) Date of Patent: Sep. 6, 2016

(54) CO-ADMINISTRATION OF AN AGENT LINKED TO AN INTERNALIZATION PEPTIDE WITH AN ANTI-INFLAMMATORY

(71) Applicant: NoNO Inc., Toronto, OT (CA)

(72) Inventors: Michael Tymianski, Toronto (CA); Jonathan David Garman, Thornhill (CA); Hong Cui, North York (CA)

(73) Assignee: NONO INC. (CA)

( * ) Notice: Subject to any disclaimer, the term of this patent is extended or adjusted under 35 U.S.C. 154(b) by 0 days.

(21) Appl. No.: 14/585,028

(22) Filed: Dec. 29, 2014

(65) Prior Publication Data

US 2015/0126460 A1 May 7, 2015

Related U.S. Application Data

(62) Division of application No. 13/377,519, filed as application No. PCT/US2010/038226 on Jun. 10, 2010, now Pat. No. 8,933,013.

(60) Provisional application No. 61/185,943, filed on Jun. 10, 2009.

(51) Int. Cl.
| | |
|---|---|
| *A61K 38/00* | (2006.01) |
| *A61K 38/02* | (2006.01) |
| *A61K 47/48* | (2006.01) |
| *A61K 31/275* | (2006.01) |

(Continued)

(52) U.S. Cl.
CPC ....... *A61K 47/48315* (2013.01); *A61K 31/275* (2013.01); *A61K 31/277* (2013.01); *A61K 38/08* (2013.01); *A61K 38/10* (2013.01); *A61K 45/06* (2013.01)

(58) Field of Classification Search
None
See application file for complete search history.

(56) References Cited

U.S. PATENT DOCUMENTS

| 7,595,297 B2 | 9/2009 | Tymianski |
| 8,080,518 B2 | 12/2011 | Tymianski et al. |

(Continued)

FOREIGN PATENT DOCUMENTS

| EP | 2 223 998 A1 | 9/2010 |
| WO | WO 00/34468 A2 | 6/2000 |

(Continued)

OTHER PUBLICATIONS

Futaki et al. Arginine-rich peptides. An abundant source of membrane-permeable peptides having potential as carriers for intracellular protein delivery. J Biol Chem. Feb. 23, 2001;276(8):5836-40.*

(Continued)

*Primary Examiner* — Satyanarayana R Gudibande
*Assistant Examiner* — Jia-Hai Lee
(74) *Attorney, Agent, or Firm* — Alston & Bird LLP

(57) ABSTRACT

The invention provides methods of delivering pharmacologic agents linked to an internalization peptide, in which an inflammatory response inducible by the internalization peptide is inhibited by co-administration of an anti-inflammatory or by linking the internalization peptide to biotin or similar molecule. Such methods are premised in part on the results described in the examples whereby administration of a pharmacological agent linked to tat at high dosages is closely followed by an inflammatory response, which includes mast cell degranulation, histamine release and the typical sequelae of histamine release, such as redness, heat, swelling, and hypotension.

4 Claims, 15 Drawing Sheets

(51) Int. Cl.
*A61K 38/08* (2006.01)
*A61K 38/10* (2006.01)
*A61K 45/06* (2006.01)
*A61K 31/277* (2006.01)

(56) References Cited

U.S. PATENT DOCUMENTS

| | | | |
|---|---|---|---|
| 8,933,013 | B2 | 1/2015 | Tymianski et al. |
| 2001/0008758 | A1 | 7/2001 | McHale et al. |
| 2002/0032154 | A1 | 3/2002 | Peyman |
| 2003/0050243 | A1 | 3/2003 | Tymianski |
| 2003/0083256 | A1 | 5/2003 | Rothbard et al. |
| 2005/0256065 | A1* | 11/2005 | Harris ............... A61K 31/704 514/37 |
| 2006/0142181 | A1 | 6/2006 | Miller |
| 2006/0148711 | A1 | 7/2006 | Lu et al. |
| 2006/0276455 | A1 | 12/2006 | Lindsberg et al. |
| 2007/0048310 | A1 | 3/2007 | Anderson |
| 2007/0225209 | A1 | 9/2007 | Roch et al. |

FOREIGN PATENT DOCUMENTS

| | | | | |
|---|---|---|---|---|
| WO | WO 01/83547 | A2 | 11/2001 | |
| WO | WO 2004/071531 | A1 | 8/2004 | |
| WO | WO2008109010 | A1 * | 9/2008 | ............ A61K 38/16 |
| WO | WO 2008/109010 | A1 | 12/2008 | |
| WO | WO 2009/006611 | A1 | 1/2009 | |
| WO | WO 2009/015385 | A1 | 1/2009 | |
| WO | WO 2009/076105 | A2 | 6/2009 | |
| WO | WO 2010/144742 | A2 | 12/2010 | |

OTHER PUBLICATIONS

Normal saline solution. 2009. www.paramedicine.com.*
Betts et al. Amino Acid Properties and Consequences of Substitutions. Bioinformatics for Geneticists; Chapter 14, pp. 289-316. 2003 John Wiley & Sons, Ltd.*
Aarts et al., "Treatment of ischemic brain damage by perturbing NMDA receptor—PSD-95 protein interactions," *Science*, 298(5594):846-850, (2002).
Bach et al., "Modified Peptides as Potent Inhibitors of the Postsynaptic Density-95/N-Methyl-D-Aspartate Receptor Interaction," *J. Med. Chem.*, 51:6450-6459, (2008).
Barr et al., "Addition of a mast cell stabilizing compound to organ preservation solutions decreases lung reperfusion injury," J. Thorac. Cardiovasc. Surg., 115(3):631-636, (1998).
Bassand et al., "Differential interaction of the tSXV motifs of the NR1 and NR2A NMDA receptor subunits with PSD-95 and SAP97," *Eur. J. Neurosci.*, 11:2031-2043, (1999).
Blom, et al, "A method for determining whether hypotension caused by novel compounds in preclinical development results from histamine release" *Journal of Pharma*, (49):31-37 (2004).
Buonaguro et al., "Effects of the Human Immunodeficiency Virus Type 1 Tat Protein on the Expression of Inflammatory Cytokines," *J. Virol.*, 66:7159-7167, (1992).
Cui et al., "PDZ Protein Interactions Underlying NMDA Receptor-Mediated Excitotoxicity and Neuroprotection by PSD-95 Inhibitors," *Neurobiology of Disease*, 27:9901-9915, (2007).

European Supplementary Search Report and European Search Opinion for application EP 08859906.3 mailed Oct. 25, 2011.
European Supplementary Search Report and European Search Opinion for application EP 10786870.5 mailed Mar. 26, 2013.
Ferry et al., "G protein-dependent activation of mast cell by peptides and basic secretagogues," *Peptides*, 23:1507-1515, (2002).
Herce, "Molecular dynamics simulations suggest a mechanism for translocation of the HIV-1 TAT peptide across lipid membranes," *Proc. Natl. Acad. Sci. U.S.A.*, 104(52):20805-20810, (2007).
Invitation to Pay Additional Fees and, Where Applicable, Protest Fee for application PCT/US08/85280 filed Dec. 2, 2008.
Keller et al., "Acute Reoxygenation Injury in the Isolated Rat Heart: Role of Resident Cardiac Mast Cells," *Circulation Research*, 63(6)1044-1052, (1988).
Kurose et al., "Ischemia/reperfusion—induced microvascular dysfunction: role of oxidants and lipid mediator," *Am. J. Physiol.*, 272(6 Pt 2):H2976-H2982, (1997).
Ling et al., "Improved outcomes in patients with acute allergic syndromes who are treated with combined H1 and H2 antagonists," Annals of Emergency Medicine, 36(5):462-468, (2000).
Mackins et al., "Cardiac mast cell-derived renin promotes focal angiotensin formation, norepinephrine release, and arrhythmias in ischemia/ reperfusion," *J. Clin. Invest.*, 116(4):1063-1070, (2006).
Marinova et al., "Translocation of dynorphin neuropeptides across the plasma membrane. A putative mechanism of signal transmission," *J. Biol. Chem.*, 280:26360-26370, (2005).
PCT Search Report and Written Opinion of the International Searching Authority for application PCT/US2010/038226 mailed Feb. 21, 2011.
PCT Search Report for application PCT/US2008/085280 mailed May 7, 2009.
Puxeddu et al., "Mast cells in allergy and beyond," *Int J Biochem Cell Biol*, 35(12)1601-1607, (2003).
Spisani et al., "Chemotactic Response of Human Monocytes to Pentapeptide Analog Derived from Immunodeficiency Virus Protein gp 120," *Inflammation*, 14:55-60, (1990).
Sun et al., "Effectiveness of PSD95 inhibitors in permanent and transient focal ischemia in the rat," *Stroke*, 39(9):2544-2553, (2008).
Takagi et al., "Altered Interaction Between PSD-95 and the NMDA Receptor Following Transient Global Ischemia," *J. Neurochemistry*, 74: 169-178, (2000).
U.S. Appl. No. 12/23,915, Requirement for Restriction/Election Sep. 24, 2009.
U.S. Appl. No. 12/323,915, Final Office Action Mailed Sep. 27, 2010.
U.S. Appl. No. 12/323,915, Non-Final Office Action Mailed Feb. 25, 2010.
U.S. Appl. No. 12/323,915, Notice of Allowance Mailed Jul. 21, 2011.
U.S. Appl. No. 13/377,519, Final Office Action Mailed Aug. 1, 2013.
U.S. Appl. No. 13/377,519, Non-Final Office Action Mailed Feb. 15, 2013.
U.S. Appl. No. 13/377,519, Notice of Allowance Mailed Jan. 9, 2014.
U.S. Appl. No. 13/377,519, Notice of Allowance Mailed Sep. 4, 2014.
U.S. Appl. No. 13/377,519, Requirement for Restriction/Election Dec. 7, 2012.

* cited by examiner

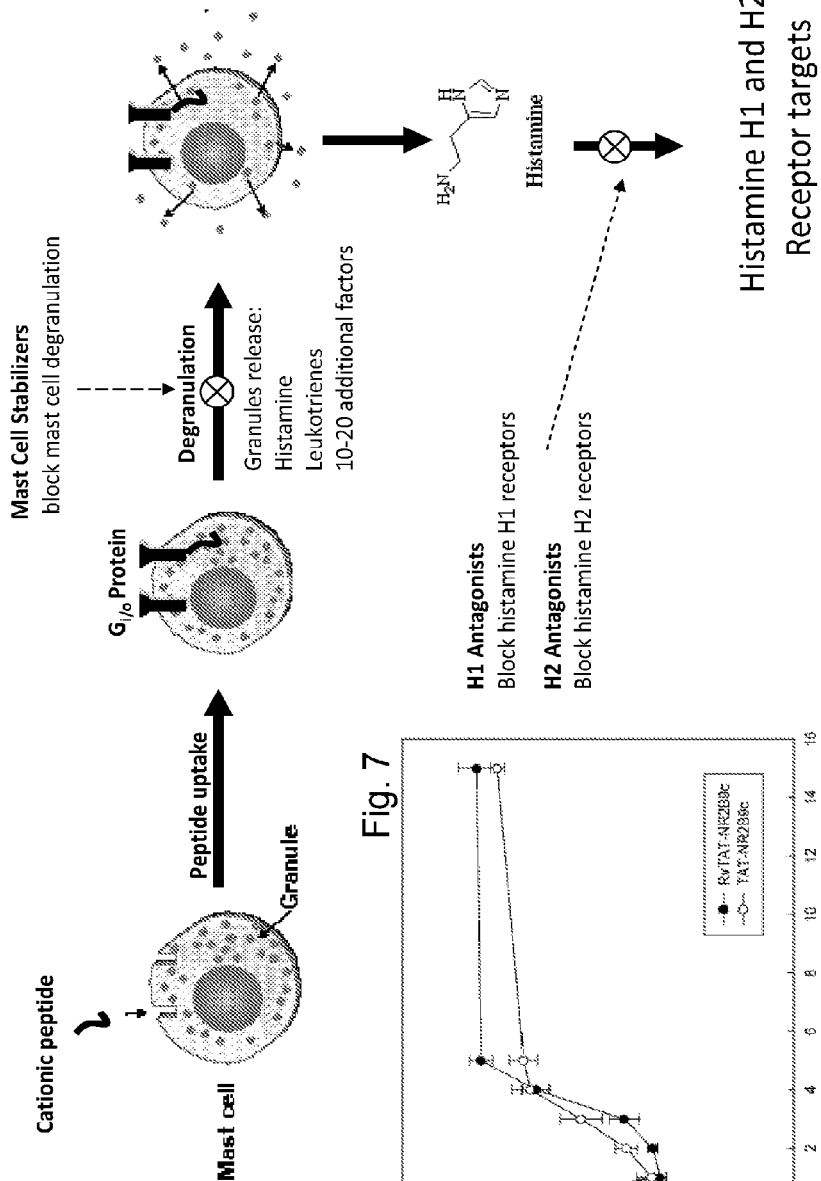

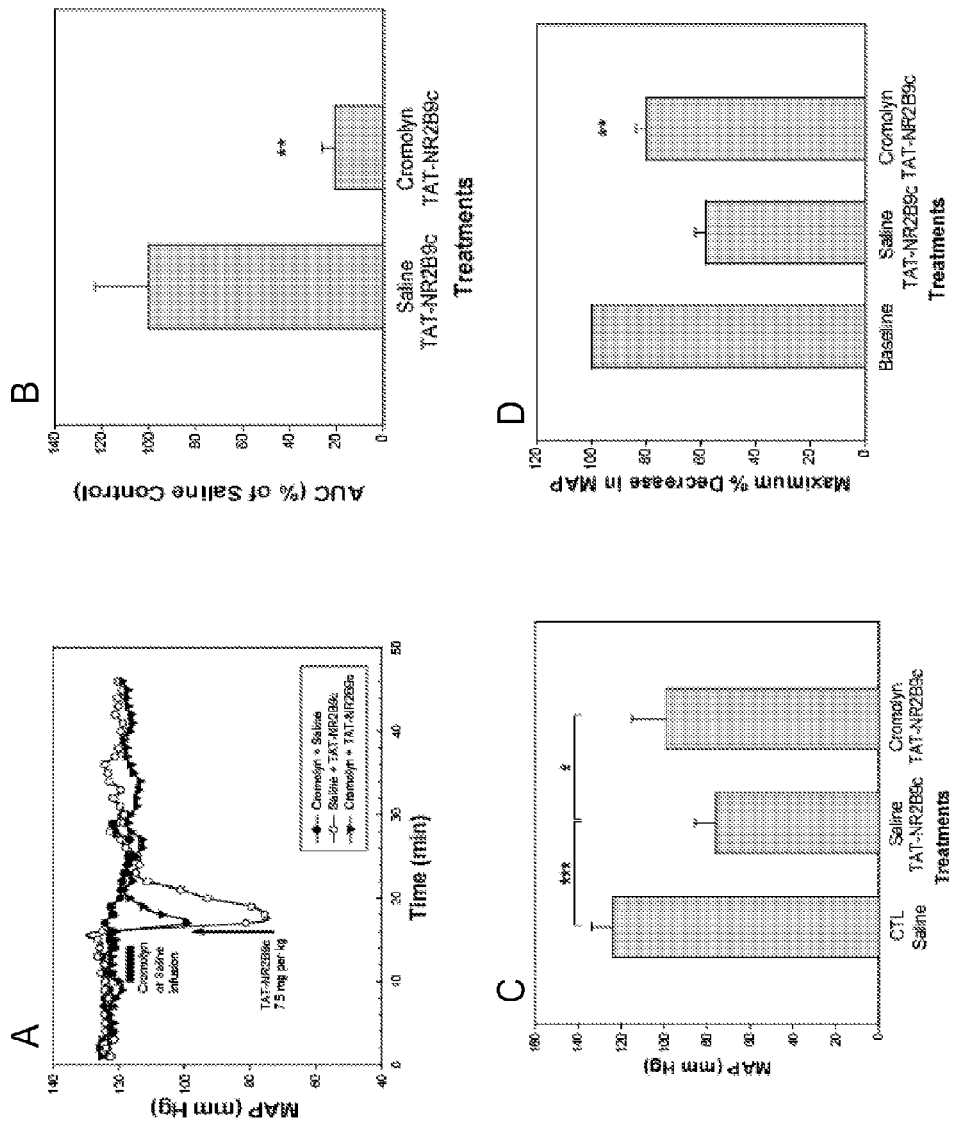
Figs. 8A-D

Fig. 8E, F
E
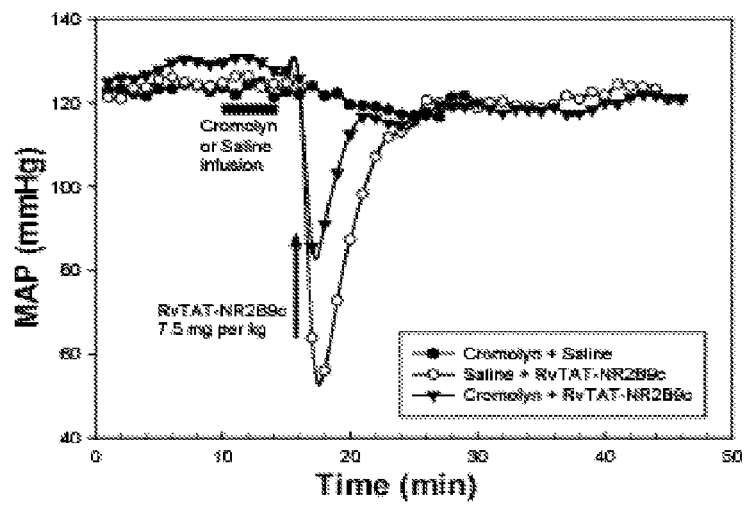
F
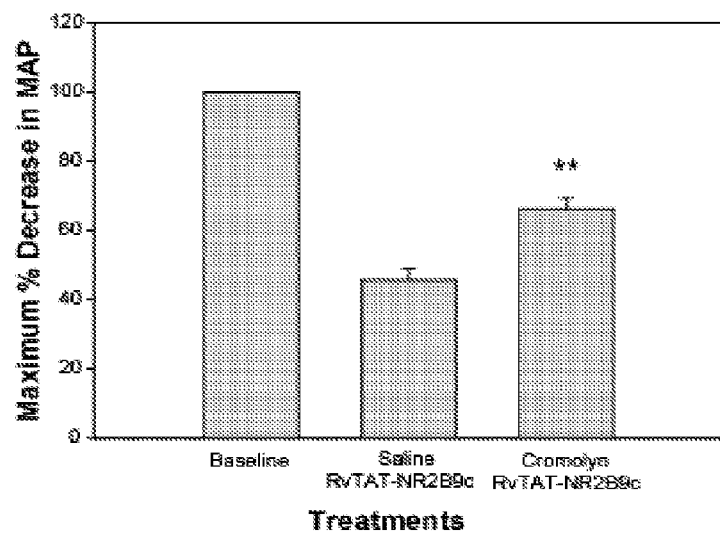

Figs. 9A-D
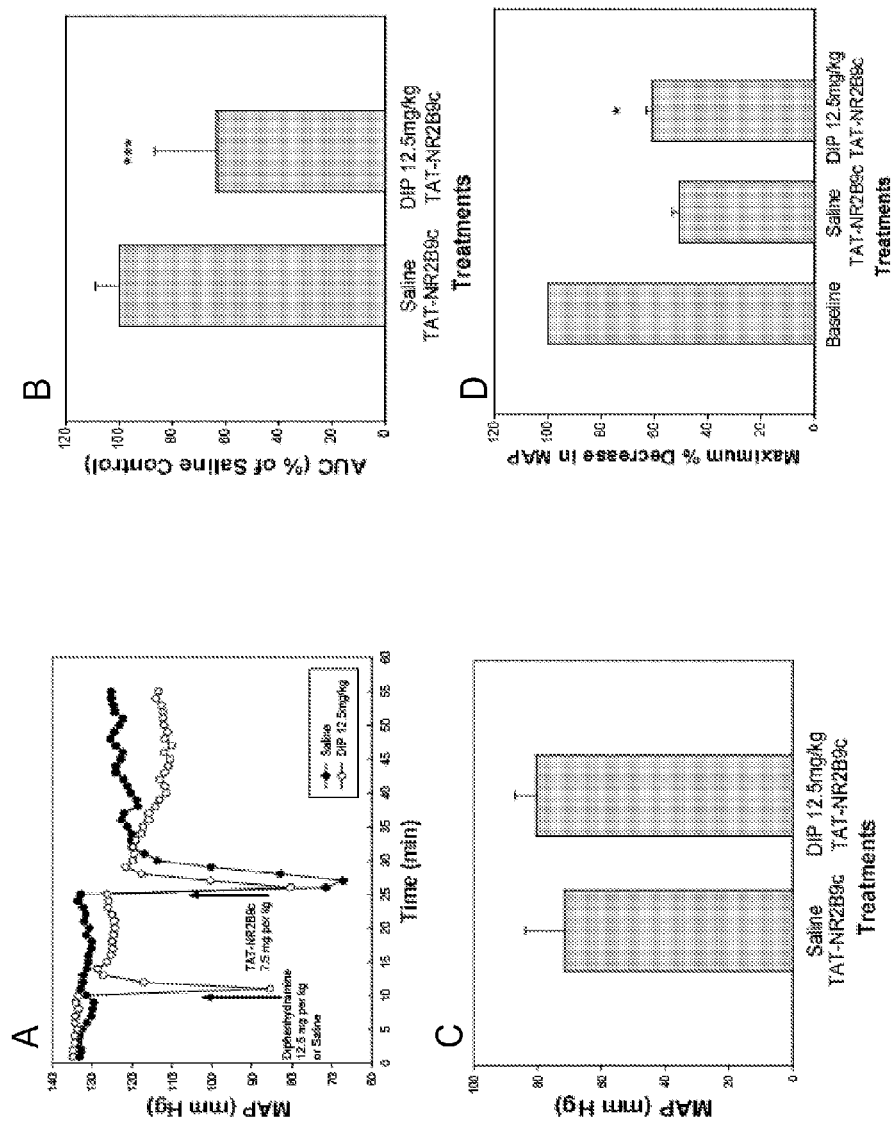

Figs. 10A-D
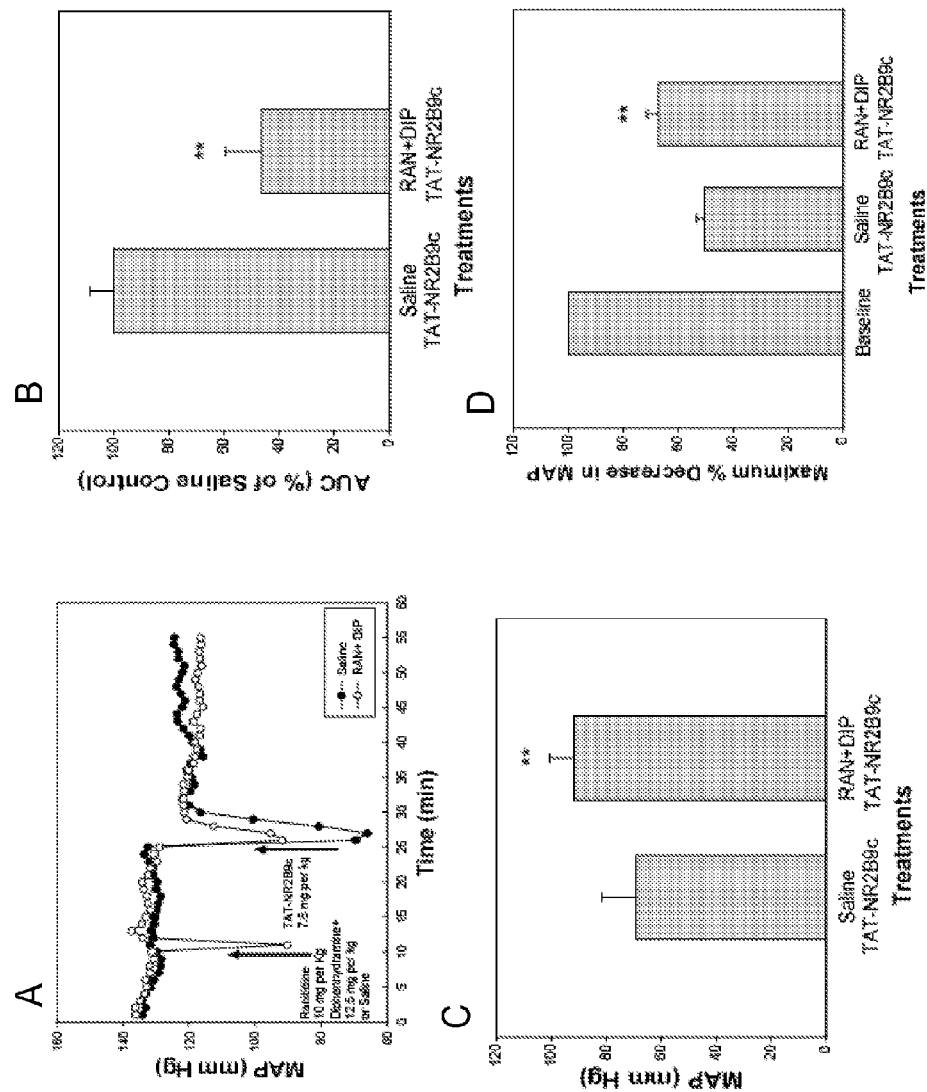

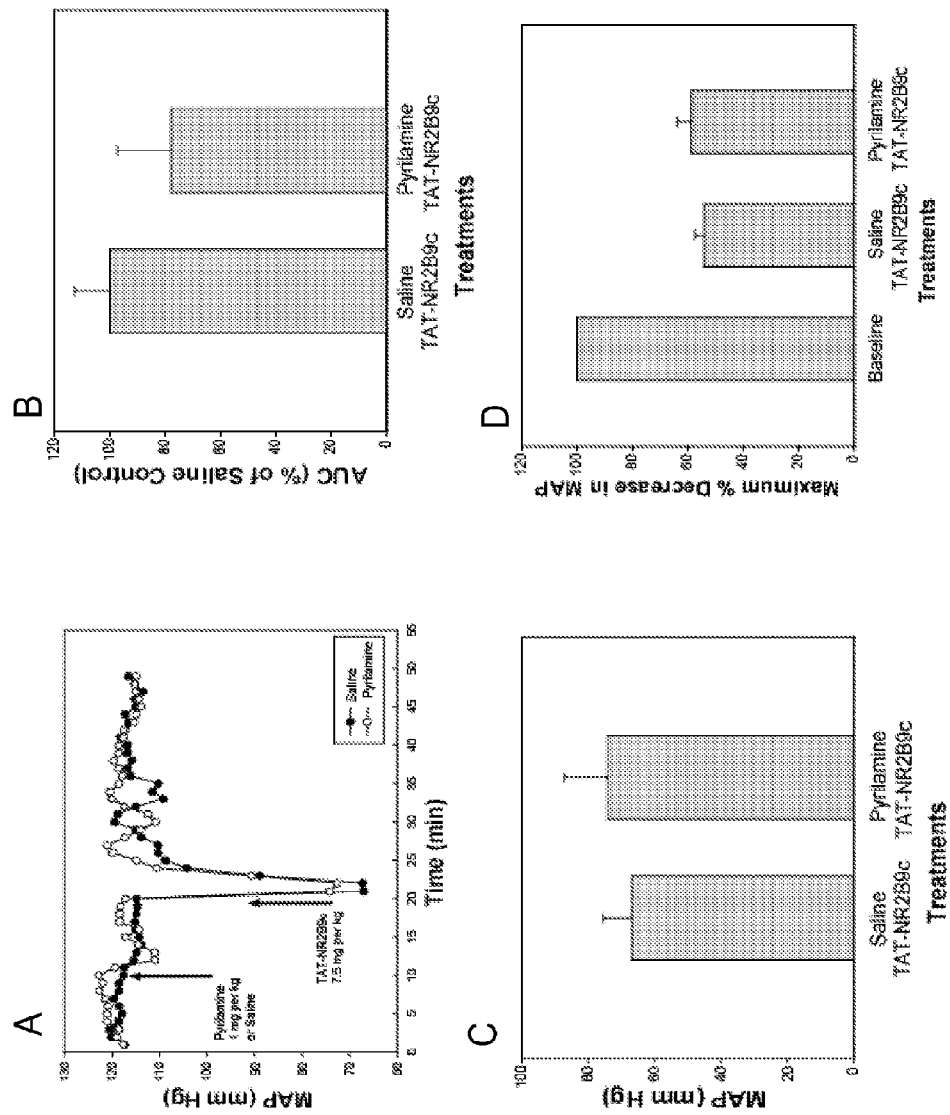
Figs. 11A-D

CO-ADMINISTRATION OF AN AGENT LINKED TO AN INTERNALIZATION PEPTIDE WITH AN ANTI-INFLAMMATORY

CROSS REFERENCE TO RELATED APPLICATIONS

The present application is a divisional of U.S. Ser. No. 13/377,519 filed Jun. 13, 2012, which is a national stage of PCT/US2010/038226 filed Jun. 10, 2010, which claims priority from U.S. 61/185,943 filed Jun. 10, 2009, each incorporated by reference in its entirety.

REFERENCE TO A SEQUENCE LISTING SUBMITTED IN A COMPUTER READABLE FORMAT

The sequence listing written in the file 456232_SEQL-ST.TXT is 18,126 bytes, and was created on Dec. 19, 2014 and is hereby incorporated by reference.

BACKGROUND OF THE INVENTION

Many drugs are required to be taken up by cells or pass through cells and/or be taken up by cellular organelles to reach their intended therapeutic target. Many larger molecules and some small ones by themselves have limited capacity to pass through cellular membranes. The capacity to pass through cellular membranes can be increased by linking a pharmacological agent to an internalization peptide (also known as protein transduction domains, or membrane translocation domains). These peptides include tat, antennapedia peptide and arginine-rich peptides. These peptides are short basic peptides present in many cellular and viral proteins and serve to mediate translocation across membranes. A common feature of these peptides is their highly cationic nature. Such peptides have been reported to facilitate uptake of many different peptide and proteins into cells, as well as oligonucleotides, peptide nucleic acids and small molecules and nanoparticles. Uptake into cells and organelles and across the blood brain barrier has been reported.

As one application of internalization peptides, a tat peptide has been linked to a peptide inhibitor of interaction between postsynaptic density-95 protein (PSD-95) and NMDARs (Aarts et al., Science 298, 846-850 (2002)). The resulting chimeric peptide was tested in a cellular and an animal model of stroke. The chimeric peptide was taken up into neuronal cells and found to reduce ischemic brain damage in the animal model. This result has led to the proposal to use peptide antagonists of PSD-95/NMDAR linked to an internalization peptide for treating stroke and other diseases mediated by excitotoxicity.

SUMMARY OF THE INVENTION

The invention provides a method of inhibiting cerebral ischemia due to endovascular surgery, comprising administering to a subject undergoing endovascular surgery a pharmacologic agent that inhibits binding of PSD95 to NDMAR 2B linked to an internalization peptide in a regime effective to inhibit cerebral ischemia; and administering to the subject a mast cell degranulation inhibitor, whereby the mast cell degranulation inhibitor can inhibit an-anti-inflammatory response inducible by the internalization peptide and/or the mast cell degranulation inhibitor is administered within a period of 30 minutes before to 15 minutes after the pharmacological agent.

The invention further provides a pharmacologic agent that inhibits binding of PSD95 to NDMAR 2B linked to an internalization peptide for use in inhibiting cerebral ischemia due to endovascular surgery in combination with a mast cell degranulation inhibitor to inhibit an inflammatory response inducible by the internalization peptide The invention further provides a mast cell degranulation inhibitor for use in inhibiting cerebral ischemia due to endovascular surgery in combination with a pharmacologic agent that inhibits binding of PSD95 to NDMAR 2B linked to an internalization peptide, wherein the mast cell degranulation inhibitor inhibits an inflammatory response inducible by the internalization peptide.

Optionally, the mast cell degranulation inhibitor is administered at the same time as or up to 15 minutes before the pharmacological agent. Optionally, the mast cell degranulation inhibitor is co-formulated with the pharmacologic agent. Optionally, the mast cell degranulation inhibitor is administered by a peripheral route. Optionally, the mast cell degranulation inhibitor and pharmacologic agent are administered intravenously. Optionally, the subject is suffering from an episode of a disease and the pharmacological agent and the mast cell degranulation inhibitor are administered once during the disease episode. Optionally, the administration of the mast cell degranulation inhibitor does not comport with a recurring regime of administering the mast cell degranulation inhibitor to the patient without the pharmacologic agent. Optionally, the internalization peptide is a tat peptide. Optionally, the tat peptide has an amino acid sequence comprising RKKRRQRRR (SEQ ID NO:51) or GRKKRRQRRR (SEQ ID NO:1). Optionally, the tat peptide has an amino acid sequence comprising YGRKKRRQRRR (SEQ ID NO:2), or FGRKKRRQRRR (SEQ ID NO:3), or GRKKRRQRRRP (SEQ ID NO:4). Optionally, the pharmacologic agent is a peptide, such as KLSSIESDV (SEQ ID NO:5).

The invention further provides a method of treating or effecting prophylaxis of a disease mediated by excitotoxicity comprising administering to a subject having or at risk of the disease and effective regime of a peptide having an amino acid sequence consisting of or comprising (RRRQRRK-KRGYKLSSIESDV SEQ ID NO:70) to treat or effect prophylaxis of the disease. Optionally, the method further comprises administering a mast cell degranulation inhibitor and/or an anti-histamine.

The invention further provides a peptide having an amino acid sequence consisting of or comprising (RRRQRRK-KRGYKLSSIESDV SEQ ID NO:70) for use in treatment or prophylaxis of disease.

The invention further provides a method of delivering a pharmacologic agent to a subject, the method comprising: administering the pharmacologic agent linked to an internalization peptide to the subject; and administering a mast cell degranulation inhibitor to the subject, whereby the lodoxamide can inhibit an inflammatory response inducible by the internalization peptide; and the mast cell degranulation inhibitor is tranilast, lodoxamide, azelastine, bepotastine, chlorzoxazone, epinastine, isoproterenol, olopatadine, pemirolast, pimecrolimus or pirbuterol.

Optionally, the mast cell degranulation inhibitor is administered at the same time as or up to 15 minutes before the pharmacological agent. Optionally, the mast cell degranulation inhibitor is co-formulated with the pharmacologic agent. Optionally the method is for treating or prophylaxis of a disease mediated by excitotoxicity in the subject. Optionally, the pharmacological agent is a PL peptide of an NMDAR receptor. Optionally, the internalization peptide is a tat peptide, for example having an amino acid sequence comprising RKKRRQRRR (SEQ ID NO:51), GRKKRRQRRR (SEQ ID NO:1), YGRKKRRQRRR (SEQ ID NO:2), FGRKKRRQRRR (SEQ ID NO:3) or GRKKRRQRRRPQ (SEQ ID NO:4).

Optionally, the disease is stroke or the subject is at risk of transient cerebral ischemic attack as a result of undergoing surgery. Optionally, the mast cell degranulation inhibitor is administered by a peripheral route. Optionally, the mast cell degranulation inhibitor is administered within a window of 30 minutes before to 15 after administering the pharmacologic agent. Optionally, the mast cell degranulation inhibitor is administered within a window of 15 minutes before to the same time as administering the pharmacologic agent. Optionally, the subject is suffering from an episode of a disease and the pharmacological agent and the mast cell degranulation inhibitor are administered once during the disease episode. Optionally, the administration of the mast cell degranulation inhibitor does not comport with a recurring regime of administering the mast cell degranulation inhibitor to the patient without the pharmacologic agent. Optionally, the mast cell degranulation inhibitor and pharmacological agent linked to the internalization peptide are co-formulated. Optionally, the co-formulation is administered intravenously.

The invention further provides a kit comprising a pharmacological agent linked to an internalization peptide, and lodoxamide. The invention further provides lodoxamide for use in inhibiting a mast cell degranulation response inducible by a pharmacologic agent linked to an internalization peptide. The invention further provides a pharmacologic agent linked to an internalization peptide for use in treatment or prophylaxis of disease in combination with lodoxamide to suppress and inflammatory response inducible by the internalization peptide. The invention further provides a pharmacologic agent that inhibits binding of PSD95 to NDMAR 2B linked to an internalization peptide in a regime effective to treat or effect prophylaxis of a diseases mediated by excitotoxicity in combination with lodoxamide to inhibit an inflammatory response inducible by the internalization peptide. The invention further provides lodoxamide for use in treatment or prophylaxis of a disease mediated by excitotoxicity in combination with a pharmacologic agent that inhibits binding of PSD95 to NDMAR 2B linked to an internalization peptide, wherein the lodoxamide inhibits an inflammatory response inducible by the internalization peptide. The invention further provides co-formulation comprising lodoxamide and a peptide having an amino acid sequence of SEQ ID NO:6 (YGRKKRRQRRRKLSSIESDV) and water. Optionally, less than 5% by weight of the lodoxamide and less than 5% by weight of the peptide is in particulate form. Optionally, the co-formulation further comprises sodium chloride at a concentration of 50-200 mM. Optionally, the concentration of lodoxamide is 0.5-1 mg/ml and the concentration of the peptide is 5-20 mg/ml The invention further provides a method of delivering a pharmacological agent linked to an internalization peptide to a population of subjects having or a risk of a disease treatable by the pharmacological agent, comprising administering the pharmacological agent linked to the internalization peptide to the subjects, wherein some subjects are administered a mast cell degranulation inhibitor to reduce an inflammatory response inducible by the internalization peptide and some subjects are not depending on the dose of the pharmacological agent linked to the internalization peptide with patients receiving a higher dose receiving the mast cell degranulation inhibitor.

The invention further provides a method of treating or effecting prophylaxis of a disease mediated by excitotoxicity comprising administering to a human subject having or at risk of the disease a peptide having an amino acid sequence of SEQ ID NO:6 (YGRKKRRQRRRKLSSIESDV) at a dose of greater or equal to 2.0 mg/kg; and administering to the subject a mast cell degranulation inhibitor, whereby the mast cell degranulation inhibitor can inhibit mast cell degranulation inducible by the internalization peptide and/or the mast cell degranulation inhibitor is administered within a period of 30 minutes before to 15 minutes after the pharmacological agent. Optionally, the dose is 2.6 mg/kg.

The invention further provides a method of delivering a pharmacological agent linked to an internalization peptide to a subject having or a risk of a disease treatable by the pharmacological agent, comprising administering the pharmacological agent linked to the internalization peptide to the subject, administering a mast cell degranulation inhibitor and an anti-histamine to reduce an inflammatory response inducible by the internalization peptide.

The invention provides methods of delivering a pharmacologic agent to a subject. The methods involve administering the pharmacologic agent linked to an internalization peptide to the subject; and administering a mast cell degranulation inhibitor to the subject, whereby the mast cell degranulation inhibitor can inhibit a mast cell degranulation inducible by the internalization peptide and/or the mast cell degranulation inhibitor is administered within a period of 30 minutes before to 15 minutes after the pharmacological agent. In some methods, the mast cell degranulation inhibitor inhibits a decline in blood pressure or skin rash induced by the internalization peptide. In some methods, the mast cell degranulation inhibitor is cromolyn. In some methods, the mast cell degranulation inhibitor is administered by a peripheral route. In some methods, the mast cell degranulation inhibitor is administered within a window of 30 minutes before to 15 minutes after administering the pharmacologic agent. In some methods, the mast cell degranulation inhibitor is administered within a window of 15 minutes before to the same time as administering the pharmacologic agent. In some methods, the subject is suffering from an episode of a disease and the pharmacological agent and the mast cell degranulation inhibitor are administered once during the disease episode. In some methods, the administration of the mast cell degranulation inhibitor does not comport with a recurring regime of administering the mast cell degranulation inhibitor to the patient without the pharmacologic agent. In some methods, the mast cell degranulation inhibitor does not cross the blood brain barrier in sufficient amounts to exert a detectable pharmacological effect in the brain when administered orally or intravenously. In some methods, the internalization peptide is a tat peptide. In some methods, the tat peptide has an amino acid sequence comprising RKKRRQRRR (SEQ ID NO:51), GRKKRRQRRR (SEQ ID NO:1), YGRKKRRQRRR (SEQ ED NO:2), FGRKKRRQRRR (SEQ ID NO:3) or GRKKRRQRRRP (SEQ ID NO:72). In some methods, the pharmacologic agent is a peptide, optionally, KLSSIESDV (SEQ ID NO:5).

The invention further provides a mast cell degranulation inhibitor for use in inhibiting mast cell degranulation inducible inducible by an internalization peptide linked to a pharmacological agent and/or for use in inhibiting a reduction in blood pressure inducible inducible by the internalization peptide, and/or for use in inhibiting a skin rash inducible by the internalization peptide. Optionally, the mast cell degranulation inhibitor is administered within a period of 15 minutes before administrating the pharmacological agent or the mast cell degranulation inhibitor and pharmacological agent are administered by intravenous infusion at the same time. Optionally, the mast cell degranulation inhibitor is administered nasally. Optionally, wherein the dose of the pharmacological agent linked to the internalization peptide is greater than 2.6 mg/kg, optionally greater than 3 mg/kg or 5 mg/kg. Optionally, the mast cell degranulation inhibitor and pharmacological agent are administered once per episode of disease. In some uses, the disease is characterized by cerebral ischemia. Optionally, the mast cell degranulation inhibitor is cromolyn and the pharmacological agent has the amino acid sequence YGRKKRRQRRRKLSSIESDV (SEQ ID NO:6).

The invention further provides a kit comprising a pharmacological agent linked to an internalization peptide, and a mast cell degranulation inhibitor.

The invention further provides methods of treating or effecting prophylaxis of a disease mediated by excitotoxicity. The method involves administering to a subject having or at risk of the disease a pharmacologic agent that inhibits binding of PSD95 to NDMAR 2B linked to an internalization peptide in a regime effective to treat or effect prophylaxis of the disease; and administering to the subject a mast cell degranulation inhibitor, whereby the mast cell degranulation inhibitor can inhibit mast cell degranulation inducible by the internalization peptide and/or the mast cell degranulation inhibitor is administered within a period of 30 minutes before to 15 minutes after the pharmacological agent. In some methods, the mast cell degranulation inhibitor inhibits a decline in blood pressure induced by the internalization peptide. In some methods, the mast cell degranulation inhibits a decline in blood pressure induced by internalization peptide. Optionally, the pharmacological agent is a PL peptide of an NMDAR receptor. Optionally, the internalization peptide is a tat peptide. Optionally, the internalization peptide has an amino acid sequence comprising RKKRRQRRR (SEQ ID NO:51), GRKKRRQRRR (SEQ ID NO:1), YGRKKRRQRRR (SEQ ID NO:2), FGRKKRRQRRR (SEQ ID NO:3) or GRKKRRQRRRPQ (SEQ ID NO:4). In some methods, the disease is stroke. In some methods, the subject is at risk of transient cerebral ischemic attack as a result of undergoing surgery. In some methods, the mast cell degranulation inhibitor is cromolyn. In some methods, the mast cell degranulation inhibitor is administered by a peripheral route. In some methods, the mast cell degranulation inhibitor is administered within a window of 30 minutes before to 15 after administering the pharmacologic agent. In some methods, the mast cell degranulation inhibitor is administered within a window of 15 minutes before to the same time as administering the pharmacologic agent. In some methods, the subject is suffering from an episode of a disease and the pharmacological agent and the mast cell degranulation inhibitor are administered once during the disease episode. In some methods, the administration of the mast cell degranulation inhibitor does not comport with a recurring regime of administering the mast cell degranulation inhibitor to the patient without the pharmacologic agent. In some methods, the mast cell degranulation inhibitor does not cross the blood brain barrier in sufficient amounts to exert a pharmacological effect in the brain when administered orally or intravenously. In some methods, the mast cell degranulation inhibitor is administered nasally, orally or intravenously.

The invention also provides in a method of delivering a pharmacologic agent linked to an internalization peptide to a subject, the improvement wherein the internalization peptide is administered with a mast cell degranulation inhibitor that can inhibit mast cell degranulation inducible by the internalization peptide and/or the mast cell degranulation inhibitor is administered within a period of 30 minutes before to 15 minutes after the pharmacological agent. Optionally, the internalization peptide is a tat peptide.

The invention further provides a method of inhibiting mast cell degranulation. The method involves administering a mast cell degranulation inhibitor to a subject who has been or will be administered a pharmacologic agent linked to an internalization peptide; whereby the anti-inflammatory agent can inhibit mast cell degranulation inducible by the internalization peptide and/or the mast cell degranulation inhibitor is administered within a period of 30 minutes before to 15 minutes after the pharmacological agent. Optionally, the mast cell degranulation inhibitor inhibits a decline in blood pressure induced by the internalization peptide. Optionally, the mast cell degranulation inhibitor inhibits development of a skin rash induced by the internalization peptide.

The invention further provides methods of delivering a pharmacologic agent to a subject. The method involves administering the pharmacologic agent linked to an internalization peptide to a subject, wherein the subject has been or will be administered a mast cell degranulation inhibitor, whereby the mast cell degranulation inhibitor inhibits mast cell degranulation induced by the internalization peptide and/or the mast cell degranulation inhibitor is administered within a period of 30 minutes before to 15 minutes after the pharmacological agent. In some methods, the mast cell degranulation inhibitor inhibits a decline in blood pressure induced by the internalization peptide.

The invention further provides methods of inhibiting inflammation inducible by a pharmacological agent linked to an internalization peptide, comprising administering a mast cell degranulation inhibitor at the same time as or up to 15 minutes before the pharmacological agent. In some methods, the pharmacological agent and mast cell degranulation inhibitor are administered at the same time by intravenous infusion. In some methods, the mast cell degranulation inhibitor is administered before the pharmacological agent.

The invention provides a method of delivering a pharmacologic agent to a subject. The method comprises administering the pharmacologic agent linked to an internalization peptide to the subject; and administering an anti-inflammatory agent to the subject, whereby the anti-inflammatory agent inhibits an inflammatory response induced by the internalization peptide. Optionally, the anti-inflammatory agent is an anti-histamine or a corticosteroid. Optionally, the internalization peptide is a tat peptide. Optionally, the tat peptide has an amino acid sequence comprising GRKKRRQRRR (SEQ ID NO:1), YGRKKRRQRRR (SEQ ID NO:2), FGRKKRRQRRR (SEQ ID NO:3), or GRKKRRQRRRPQ (SEQ ID NO:4). Optionally, the pharmacologic agent is a peptide. Optionally, the pharmacologic agent is KLSSIESDV (SEQ ID NO:5).

The invention also provides for use of an anti-inflammatory agent in the manufacture of a medicament to inhibit an inflammatory response induced by an internalization peptide linked to a pharmacological agent.

The invention also provides a kit comprising a pharmacological agent linked to an internalization peptide, and an anti-inflammatory agent that inhibits an inflammatory response induced by the internalization peptide.

The invention also provides an internalization peptide linked to biotin having reduced capacity to induce an inflammatory response compared to the internalization peptide without the biotin.

The invention also provides a method of delivering a pharmacologic agent to a subject, the method comprising administering the pharmacologic agent linked to an internalization peptide to the subject; wherein the internalization peptide is biotinylated, and the biotinylation reduces the capacity of the internalization peptide to induce an inflammatory response relative to the internalization peptide without the biotin.

The invention also provides a method of treating or effecting prophylaxis of a disease mediated by excitotoxicity comprising administering to a subject having or at risk of the disease a pharmacologic agent that inhibits binding of PSD95 to NDMAR 2B linked to an internalization peptide in a regime effective to treat or effect prophylaxis of the disease; and administering to the subject an anti-inflammatory agent, whereby the anti-inflammatory agent inhibits an inflammatory response induced by the internalization peptide. Optionally, the pharmacological agent is a PL peptide of an NMDAR receptor. Optionally, the internalization peptide is a tat peptide. Optionally, the internalization peptide has an amino acid sequence comprising GRKKRRQRRR (SEQ ID NO:1), YGRKKRRQRRR (SEQ ID NO:2), FGRKKRRQRRR (SEQ ID NO:3) or GRKKRRQRRPQ (SEQ ID NO:4). Optionally, the subject is female. Optionally, the disease is stroke. In some methods, the subject is at risk of transient cerebral ischemic attack as a result of undergoing heart surgery.

The invention further provides a method of treating or effecting prophylaxis of a disease mediated by excitotoxicity comprising administering to a subject having or at risk of the disease a pharmacologic agent that inhibits binding of PSD95 to NDMAR 2B linked to an internalization peptide in a regime effective to treat or effect prophylaxis of the disease; wherein the internalization peptide is biotinylated, and the biotinylation reduces the capacity of the internalization peptide to induce an inflammatory response.

The invention further provides a method of treating or effecting prophylaxis of a disease mediated by excitotoxicity comprising administering to a female subject having or at risk of the disease a pharmacologic agent that inhibits binding of PSD95 to NDMAR 2B linked to an internalization peptide in a regime effective to treat or effect prophylaxis of the disease. Optionally, the internalization peptide is a tat peptide.

The invention further provides an improvement in a method of delivering a pharmacologic agent linked to an internalization peptide to a subject, wherein either the internalization peptide is biotinylated or administered with an immunosuppressive that inhibits an inflammatory response induced by the internalization peptide. Optionally, the internalization peptide is a tat peptide.

The invention further provides a method of inhibiting an inflammatory response, the method comprising: administering an anti-inflammatory agent to a subject who has been or will be administered a pharmacologic agent linked to an internalization peptide; whereby the anti-inflammatory agent inhibits an inflammatory response induced by the internalization peptide.

The invention further provides a method of delivering a pharmacologic agent to a subject, the method comprising: administering the pharmacologic agent linked to an internalization peptide to a subject, wherein the subject has been or will be administered an anti-inflammatory agent, whereby the anti-inflammatory agent inhibits an inflammatory response induced by the internalization peptide.

BRIEF DESCRIPTION OF THE DRAWINGS

FIG. 7 shows reduction in blood pressure after administration of Tat-NR2B9c or Rv-Tat-NR2B9c to rats.

FIGS. 8A-D show changes mean arterial pressure (MAP) following administration of cromolyn and Tat-NR2B9c. FIG. 8A shows a time course, FIG. 8B shows percentage change in area under the curve (AUC), FIG. 8C shows MAP values after treatment with peptide transduction domain in the presence and absence of Cromolyn, FIG. 8D shows the percentage of MAP trough after treatment relative to MAP before treatment. FIGS. 8E (time course) and 8F (bar chart) show cromolyn has a similar effect with Rv-Tat-NR2B9c.

FIGS. 9A-D provide similar data to FIGS. 8A-D except cromolyn is replaced with dephenhydramine.

FIGS. 10A-D provide similar data to FIGS. 8A-D except cromolyn is replaced by pyrilamine.

FIGS. 11A-D provide similar data to FIGS. 8A-D except cromolyn is replaced with a combination of diphenhydramine and Ranitidine.

FIG. 12 is a schematic showing a cationic peptide, such as tat, inducing mast cell degranulation and consequent release of histamine and other factors, which cause diverse effects including a lowering of blood pressure. Mast cell granulation inhibitors (also known as mast cell stabilizers) inhibit the degranulation of mast cells and consequent release of histamine and other molecules by the mast cells.

DETAILED DESCRIPTION

Definitions

Figure 1:
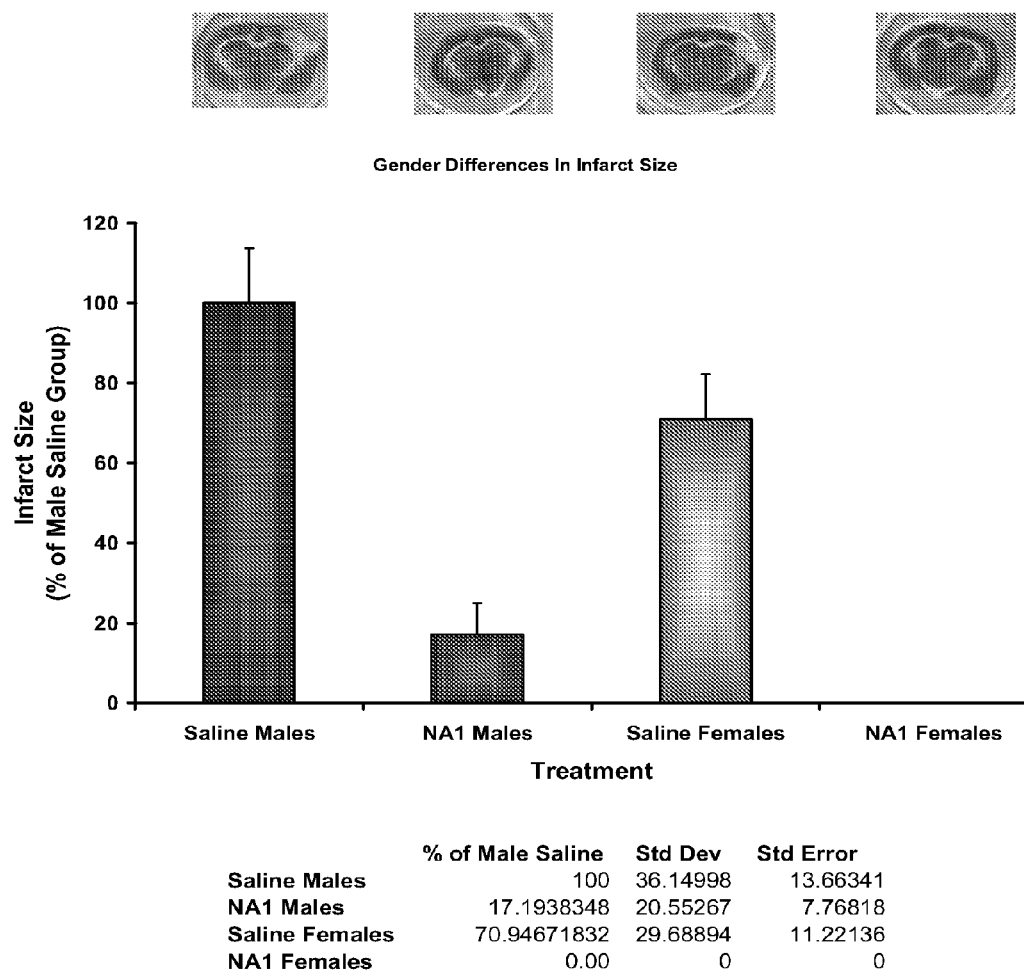
FIG. 1: Gender difference in infarct size in the P3V0 model of stroke in the rat. Saline males: male stroke rats treated with saline (control). Tat-NR2B9c males: Male stroke rats treated with Tat-NR2B9c, i.e., the peptide YGRKKRRQRRRKLSSIESDV (SEQ ID NO:6), containing both Tat sequence and the 9 carboxy-terminal amino acids of the NR2B subunit. Saline females: female stroke rats treated with saline (control). Tat-NR2B9c females: Female stroke rats treated with Tat-NR2B9c, i.e., the peptide YGRKKRRQRRRKLSSIESDV (SEQ ID NO:6), containing both Tat sequence and 9 carboxy-terminal amino acids of the NR2B subunit. Y axis: Size of infarct, measured (in percentage terms) relative to size of infarct in male rats treated with saline alone)

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

The term "PDZ domain" refers to a modular protein domain of about 90 amino acids, characterized by significant sequence identity (e.g., at least 60%) to the brain synaptic protein PSD-95, the *Drosophila septate* junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA. The term thus includes the various subunit forms described herein. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species. The term isolated or purified does not necessarily exclude the presence of other components intended to act in combination with an isolated species. For example, an internalization peptide can be described as isolated notwithstanding that it is linked to an active peptide.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

Individual peptidomimetic residues can be joined by peptide bonds, other chemical bonds or coupling means, such as, e.g., glutaraldehyde, N-hydroxysuccinimide esters, bifunctional maleimides, N,N-dicyclohexylcarbodiimide (DCC) or N,N-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, NY).

Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R—N═C═N—R═) such as, e.g., l-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110: 1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114:10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777. Secondary structures of polypeptides can be analyzed by, e.g., high-field.sup.1H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors, for instance NMDAR 2B.

The term "subject" includes humans and veterinary animals, such as mammals.

The term "agent" includes any element, compound, or entity, including, e.g., pharmaceutical, therapeutic, pharmacologic, cosmeceutical, drug, toxin, natural product, synthetic compound, chemical compounds. Agents can be biologics (e.g., peptides, petidomimetics, or antibodies) or organic small molecules (usually less than 500 Da) among others.

The term "pharmacologic agent" means an agent having a pharmacological activity. Agents include compounds that are known (i.e., approved by FDA or similar body in other countries) drugs, compounds for which pharmacological activity has been identified but which are undergoing further therapeutic evaluation. A chimeric agent comprises a pharmacologic agent linked to an internalization peptide. An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A tat peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. The amino acids of a tat peptide can be derivatized with biotin or similar molecule to reduce an inflammatory response, as described further below.

Co-administration of a pharmacological agents linked to an internalization peptide and an anti-inflammatory agent means that the two agents are administered sufficiently proximately in time that the anti-inflammatory agent can inhibit an inflammatory response inducible by the internationalization peptide.

Statistically significant refers to a p-value that is <0.05, preferably <0.01 and most preferably <0.001.

I. General

The invention provides methods of delivering pharmacologic agents linked to an internalization peptide, in which an inflammatory response inducible by the internalization peptide is inhibited by co-administration of an anti-inflammatory or by linking the internalization peptide to biotin or similar molecule. Such methods are premised in part on the results described in the examples whereby administration of a pharmacological agent linked to tat at high dosages is closely followed by an inflammatory response, which includes mast cell degranulation, histamine release and the typical sequelae of histamine release, such as redness, heat, swelling, and hypotension. Although practice of the methods of the invention is not dependent on an understanding of mechanism, it is believed that the mast cell degranulation is triggered by direct interaction between the cationic tat peptide and mast cells rather than being triggered by an IgE antibody response. The inflammatory response can be inhibited by co-administering an anti-inflammatory agent, particularly a mast cell degranulation inhibitor, such as cromolyn, with the pharmacological agent linked to tat or other internalization peptide. Other anti-inflammatory agents including anti-histamines and corticosteriods can also be used. Alternatively, the inventors have found that the capacity of internalization peptides to induce an inflammatory response can be reduced by linking them to biotin or similar molecule.

The invention further provides method of treating or effecting prophylaxis of diseases characterized by excitotoxicity, such as stroke. Such diseases can be treated using a pharmacologic agent that inhibits interaction between NMDARs with postsynaptic density 95 protein linked to an internalization peptide. Preferably, in such methods, the pharmacologic agent is co-administered with an anti-inflammatory agent, preferably a mast cell granulation inhibitor, such as cromolyn, to inhibit an immune response inducible by the internalization peptide, or the internalization peptide is linked to biotin or similar molecule, for the reasons discussed above. Irrespective whether an anti-inflammatory agent or biotinylated internalization peptide is used in such methods, the treatment or prophylaxis can be administered to both male and female subjects. The administration to female subjects is premised in part on results described in the example in which the treatment in a rat model of stroke was found to be at least as effective in female subjects as male. The feasibility of administering a pharmacological agent that inhibits interactions between PSD95 and NMDAR to a female subject contrasts with previous results in which inhibitors of nNOS were found ineffective to treat excitotoxic disease in female subjects. Administration of nNOS inhibitors were reported to protect against damaging effects of stroke in male rats, but increased cell injury in female rats in an MCAO model. McCullough et al., *Journal of Cerebral Blood Flow & Metabolism*, 25: 502-512 (2005).

II. Pharmacologic Agents

Internalization peptides can be linked to any pharmacologic agent to promote uptake of the agent through cell membranes, intracellular membranes such as the nuclear membrane, and/or the blood brain barrier. The attachment of an internalization peptide to a pharmacologic agent improves bioavailability at the intended site relative to use of the pharmacologic agent alone. The increased delivery due to the attached internalization peptides can allow decreased doses of pharmacologic agents, effective targeting of pharmacologic agents to a specific cell compartment such as the nucleus, and/or reduced toxicity due to the use of lower doses.

Internalization peptides are particularly useful for pharmacologic agents that are required to enter cells and/or the nucleus. Pharmacologic agents that have poor bioavailabilty, high dosages or short half-lives, or neuroactive drugs that need to cross the blood brain barrier to exert activity, are especially suitable for attachment of internalization peptides. Peptides are one type of pharmacologic agent that are amenable to attachment of internalization, for instance through the use of a peptide bond that results in a chimeric peptide comprising an amino acid sequence derived from the pharmacologic agent, and an amino acid sequence of the internalization peptide. Nucleic acids, and small organic molecules (less than 500 Da) are other examples of compounds that can be linked to internalization peptides.

Some guidance for selection of pharmacologic agents, methods for attachments and use thereof is provided by the scientific and patent literature relating to internalization peptides, such as tat (see, e.g., U.S. Pat. No. 6,316,003 and U.S. Pat. No. 5,804,604). The table below lists the names of pharmacologic agents (some of which are approved drugs), the disorders they are useful for treating, whether the disease is acute or chronic, the routes of administration of drugs (to the extent established) and comments on problems with existing drugs that may in part be overcome by the improved transport through membranes conferred by an internalization peptide.

TABLE 1

| Pharmacologic agent | Disease | Acute/ chronic | Route of admin | Comment | Reference |
| --- | --- | --- | --- | --- | --- |
| Phenobarbitol (luminal sodium) | Epilepsy | | IV/oral | Dependence, tolerance issues, interactions, | Motamedi & Meador (2006) Curr Neurol Neurosci Rep, |

TABLE 1-continued

| Pharmacologic agent | Disease | Acute/ chronic | Route of admin | Comment | Reference |
|---|---|---|---|---|---|
| | | | | side effects, birth defects | 6(4): 341-6. Drugs.com |
| Primidone (myidone, mysoline) | Epilepsy | | Oral | Side effects, interactions | Koristkova, et al (2006) Int J Clin Pharmacol Ther, 44(9): 438-42. Drugs.com |
| Diazepam (valium) | Anxiety | | IP/oral | Dependence, side effects, interactions | Beard, et al (2003) Health Technol Assess, 7(40): iii, ix-x, 1-111. Drugs.com |
| Dopamine | Parkinson's | | | Cannot cross BBB, side effects | Ahlskog (2001) Neurol Clin, 19(3): 579-605. Drugs.com |
| Levodopa | Parkinson's | | | Degraded before BBB, side effects, halflife = 1.5 hrs | Nyholm (2006) Clin Pharmacokinet, 45(2): 109-36. USPTO.gov (U.S. Pat. No. 7,160,913) |
| Apomorphine | | | IP | Short half-life | Nyholm (2006) Clin Pharmacokinet, 45(2): 109-36. Drugs.com |
| Tirilazad mesylate (Freedox) | Stroke | | IP | Low efficacy, phase III stopped | Hickenbottom & Grotta (1998) Semin Neurol 18(4): 485-92. Strokecenter.org |
| Cyclosporine (Gengraf) | Immune suppression | | IP | Peptide, 5-18 hr halflife | Kees, et al (2006) Ther Drug Monit, 28(3): 312-20. Drugs.com |
| Vacomycin | Antibiotic | | IP | Peptide, low uptake, 4-6 hr halflife | de Hoog, et al (2004) Clin Pharmacokinet, 43(7): 417-40. Drugs.com |
| Lisinopril (Prinivil) | Hypertension | | IP/oral | Peptide, poor BBB crossing, 12 hr halflife | Tan, et al (2005) Am J Hypertens, 18(2): 158-64. Drugs.com |
| Azidothymidine (AZT, zidoridine, combivir) | Antiviral | | Oral | Poor BBB crossing, 05-3 hr halflife, hematologic toxicology | Spitzenberger, et al (2006) J Cereb Blood Flow Metab, Oct 25, Epub ahead of print. Drugs.com |
| Piracetam | Pain/ epilepsy | | | Cannot cross BBB | Loscher & Potschka (2002) J Pharmacol Exp Ther, 301(1): 7-14. USPTO.gov (U.S. Pat. No. 7,157,421) |
| Natrecor (BNP peptide) | Cardio-renal decompensation syndrome | | IV | Unknown efficacy | Feldman & Sun (2004) Heart Fail Rev, 9(3): 203-8. Clinicaltrials.gov |
| AVR-118 (peptide) | Cancer palliative | | Sub- cutaneous | Unknown efficacy, unknown dosage | Clinicaltrials.gov |
| Oxytocin (peptide) | Mood disorders | | IV/IM | Interactions, unknown dosage | Swaab, et al (2005) Ageing Res Rev, 4(2): 141-94. Drugs.com |
| Pravastatin (Pravachol) | MS | | Oral | Unknown efficacy, low bioavailability | Hatanaka (2000) Clin Pharmacokinet, 39(6): 397-412. Clinicaltrials.gov |

TABLE 1-continued

| Pharmacologic agent | Disease | Acute/ chronic | Route of admin | Comment | Reference |
|---|---|---|---|---|---|
| Remifentanil | Pain, burn | | IV | 3.5 min halflife, metabolized by unknown esterase | Scott & Perry (2005) Drugs, 65(13): 1793-1823. Clinicaltrials.gov |
| Neurotensin | Schizophrenia, Parkinson's, addiction | | | 13AA peptide, easily degraded, cannot cross BBB | Boules, et al, (2006) Peptides, 27(10): 2523-33. |
| GDNF (glial derived neurotrophic factor) | Parkinson's | Chronic | Intra-parenchymal | Peptide, Cannot cross BBB | Grondin, et al (2003) Prog Drug Res, 61: 101-23. |
| Protease inhibitors lopinavir ritonavir saquinavir darunavir atazanavir amprenavir | HIV | | Oral | All HIV protease inhibitors suffer from the acute capacity of HIV to mutate, generating drug resistant HIV strains | Oldfield & Plosker (2006) Drugs 66(9): 1275-99. Porter & Charman (2001) Adv Drug Deliv Rev, Oct 1; 50 Suppl 1: S127-47. Piacenti (2006) Pharmacotherapy 26(8): 1111-33. |
| Dihydroergotamine | Migraine | | IV, IM, sub-Q | Interactions cause peripheral ischemia, 9 hr halflife | Modi & Lowder (2006) Am Fam Physician 73(1): 72-8. |
| Sporamax (itaconazole) | Antifungal | | Oral | Drug resistance eventually develops, congestive heart failure in some populations | Wang & Remold (2006) Cardiol Rev 14(5): 223-6. |
| Protein Kinase C inhibitors | Acute myocardial infarction, stroke, ischemia, reperfusion injury | | | | US pat publications 20050267030, 20060148702, 20060293237, 20050215483, 20040204364, 20040009922 |
| AII-7 | Cancer, breast cancer | Chronic | | Peptidomimetic that blocks Erbb2 intracellular domain and increases taxol sensitivity | Kunz et al, Mol Cancer Res 2006; 4(12): 983-98 |
| CRAMP peptide | Salmonella infection | | | Intracellular anti-microbial peptide that reduces Salmonella replication | Rosenberger, CM. PNAS| Feb. 24, 2004|vol. 101| no. 8|2422-2427 |
| Sodium channel peptide | May reduce muscle spasms (epilepsy, restless leg, Parkinson's, etc) | | | Peptide corresponding to the short intracellular segment between homologous transmembrane domains III and IV of sodium channel alpha subunit slowed inactivation | Vassilev, Science (1988) 241: 1658-6 |
| Aptamer KDI1 | Blocks EGF signaling - possible anti cancer | | | | Buerger. J. Biol. Chem., Vol. 278, Issue 39, 37610-37621, Sep. 26, 2003 |

TABLE 1-continued

| Pharmacologic agent | Disease | Acute/chronic | Route of admin | Comment | Reference |
|---|---|---|---|---|---|
| RNA/gene therapy | | | | Transporter peptides can be used to bring in RNAs or siRNA/RNAi for treatment | Turner et al (2007) Blood Cells Mol Dis, 38(1): 1-7. |

One class of agents of particular interest inhibits interactions between PSD-95 and one or more NMDARs. Such agents are useful for reducing damaging effects of stroke and other neurological conditions mediated at least in part by NMDAR excitotoxicity. Such agents include peptides having an amino acid sequence including or based on the PL motif of a NMDA Receptor or PDZ domain of PSD95. Such peptides can also or alternatively inhibit interactions between PSD-95 and nNOS and other glutamate receptors (e.g., kainite receptors or AMPA receptors). Preferred peptides inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below:

TABLE 2

NMDA Receptors With PL Sequences

| Name | GI or Acc# | C-terminal 20mer sequence | C-terminal 4mer sequence | PL? | internal PL ID |
|---|---|---|---|---|---|
| NMDAR1 | 307302 | HPTDITGPLNLSDPSVSTVV (SEQ ID NO: 13) | STVV (SEQ ID NO: 27) | X | AA216 |
| NMDAR1-1 | 292282 | HPTDITGPLNLSDPSVSTVV (SEQ ID NO: 13) | STVV (SEQ ID NO: 27) | X | AA216 |
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 29) | X | AA180 |
| NMDAR3 | 560546 | FNGSSNGHVYEKLSSIESDV (SEQ ID NO: 11) | ESDV (SEQ ID NO: 12) | X | AA34.1 |
| NMDAR3A | 17530176 | AVSRKTELEEYQRTSRTCES (SEQ ID NO: 16) | TCES (SEQ ID NO: 30) | | |
| NMDAR2B | 4099612 | FNGSSNGHVYEKLSSIESDV (SEQ ID NO: 11) | ESDV (SEQ ID NO: 12) | X | |
| NMDAR2A | 558748 | LNSCSNRRVYKKMPSIFSDV (SEQ ID NO: 17) | ESDV (SEQ ID NO: 12) | X | AA34.2 |
| NMDAR2D | 4504130 | GGDLGTRRGSAHFSSLESEV (SEQ ID NO: 18) | ESEV (SEQ ID NO: 29) | X | |
| Glutamate receptor delta 2 | AF009014 | QPTPTLGLNLGNDPDRGTSI (SEQ ID NO: 19) | GTSI (SEQ ID NO: 31) | X | |

TABLE 2-continued

NMDA Receptors With PL Sequences

| Name | GI or Acc# | C-terminal 20mer sequence | C-terminal 4mer sequence | PL? | internal PL ID |
|---|---|---|---|---|---|
| Glutamate receptor 1 | I28953 | MQSLPCMSHSSGMPLGATGL (SEQ ID NO: 20) | ATGL (SEQ ID NO: 32) | X | |
| Glutamate receptor 2 | L20814 | QNFATYKEGYNVYGIESVKI (SEQ ID NO: 21) | SVKI (SEQ ID NO: 33) | X | |
| Glutamate receptor 3 | AF167332 | QNYATYREGYNVYGTESVKI (SEQ ID NO: 22) | SVKI (SEQ ID NO: 33) | X | |
| Glutamate receptor 4 | U16129 | HTGTAIRQSSGLAVIASDLP (SEQ ID NO: 23) | SDLP (SEQ ID NO: 34) | | |
| Glutamate receptor 5 | U16125 | SFTSILTCHQRRTQRKETVA (SEQ ID NO: 24) | ETVA (SEQ ID NO: 35) | X | |
| Glutamate receptor 6 | U16126 | EVINMHTFNDRRLPGKETMA (SEQ ID NO: 25) | ETMA (SEQ ID NO: 36) | X | |
| Glutamate receptor 7 | U16127 | RRLPGKDSMACSTSLAPVFP (SEQ ID NO: 26) | PVFP (SEQ ID NO: 37) | | |

Some peptides inhibit interactions between PSD-95 and multiple NMDAR subunits. In such instances, use of the peptide does not necessarily require an understanding of the respective contributions of the different NMDARs to excitatory neurotransmission. Other peptides are specific for a single NMDAR. Similarly, if an agent characterized as inhibiting one interaction (e.g., PSD-95 and NMDAR) inherently inhibits another interaction (e.g., PSD-95 and nNOS), uses or methods employing the agent can be effected by a mechanism that involves either or both inhibitions.

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] (SEQ ID NO:38) at their C-terminus. Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides are KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide) are preferred. In some such peptides, all amino acids are from the C-terminus of an NMDA receptor (not including amino acids from an internalization peptide).

Other peptides that inhibit interactions between PDS95 and NDMARs include peptides from PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1):71-82 (1997) (human sequence) or NP_031890.1, GI:6681195 (mouse sequence) or corresponding regions of other species variants.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3,4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 has described a series of analogs of NR2B9c. PDZ-binding activity is exhibited by peptides having only three C-terminal amino acids (SDV). Bach also reports analogs having an amino acid sequence comprising or consisting of YtSXV (SEQ ID NO:68), wherein t and S are alternative amino acids, Y is selected from among E, Q, and A, or an analogue thereof, X is selected from among A, Q, D, N, N-Me-A, N-Me-Q, N-Me-D, and N-Me-N or an analogue thereof. Optionally the peptide is N-alkylated in position P3 position (third amino acid from C-terminus, i.e., the tS position). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseisslk-rrrqrrkkrgyin (SEQ ID NO: 69) (lower case letters indicating D amino acids), and reports it to be effective in inhibiting cerebral ischemia. Another effective peptide described herein is Rv-Tat-NR2B9c (RRRQRRK-KRGYKLSSIESDV SEQ ID NO:70).

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. Int. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:71) from the C-terminus of NMDAR 2B was effective in inhibiting binding of NMDAR 2B to PSD95. Optionally, about 2-10 copies of a PEG can be joined in tandem as a linker.

Appropriate pharmacological activity of peptides, peptidomimetics or other agent can be confirmed, if desired, using the animal model described in the Examples. Optionally, peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 µM, 25 µM, 10 µM, 0.1 µM or 0.01 µM in such an assay. Preferred peptides typically have an 1050 value of between 0.001-1 µM, and more preferably 0.05-0.5 or 0.05 to 0.1 µM.

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Pharmacological agents also include small molecules that inhibit interactions between PSD95 and NMDAR 2B, and/or other interactions described above. Suitable small-molecule inhibitors are described in WO 07/079406 and 60/947,892 filed on Jul. 3, 2007, each incorporated by reference in its entirety. These molecules were identified by in silico screening of a compound library for binding to PSD95, and binding of exemplary compounds was verified experimentally.

Many appropriate compounds are described in U.S. Provisional App. No. 60/947,883, hereby incorporated by reference in its entirety. An exemplary class of suitable compounds are of the formula:

wherein $R^1$ is a member selected from the group consisting of cyclohexyl substituted with 0-4 $R^7$, phenyl substituted with 0-4 $R^7$, —$(CH_2)_u$—$(CHR^8R^9)$, a branched $C_{1-6}$ alkyl (isopropyl, isobutyl, 1-isopropyl-2-methyl-butyl, 1-ethyl-propyl), and —NH—C(O)—$(CR^{10}R^{11})_v$H;

each $R^7$ is independently a member selected from the group consisting of $C_{1-6}$ alkyl, $C_{1-6}$ alkoxy, —C(O)$R^{12}$, OH, COOH, —NO, N-substituted indoline and a cell membrane translocation peptide;

each $R^8$ and $R^9$ is independently selected from the group consisting of H, OH, cyclohexane, cyclopentane, phenyl, substituted phenyl and cyclopentadiene;

each $R^{10}$ and $R^{11}$ is independently selected from the group consisting of H, cyclohexane, phenyl and a cell membrane translocation peptide;

$R^{12}$ is a member selected from the group consisting of $C_{1-6}$ alkyl and aryl; and each of u and v are independently from 0 to 20;

wherein one of $R^2$, $R^3$, $R^4$, $R^5$ and $R^6$ is —COOH, and wherein the remainder of $R^2$, $R^3$, $R^4$, $R^5$ and $R^6$ are each independently selected from the group consisting of F, H, OCH$_3$ and CH$_3$.

One such compound is 0620-0057, the structure of which is:

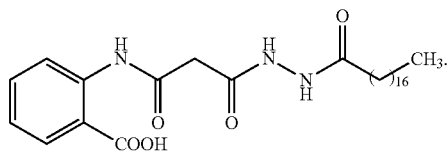

0620-0057

III. Internalization Peptides

Internalization peptides, also known as cell membrane transduction peptides or cell penetrating peptides, are a well-known class of relatively short (e.g., 5-30 amino acids) peptides that allow many cellular or viral proteins to traverse membranes. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and *Pseudomonas aeruginosa* exotoxin A (ETA). Other examples are described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005) (all incorporated by reference).

A preferred internalization peptide is tat from the HIV virus. A tat peptide reported in previous work comprises or consists of the standard amino acid sequence YGRK-KRRQRRR (SEQ ID NO:2) found in HIV Tat protein. If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)₄ (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRK-KRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present.

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRK-KRRQRRR (SEQ ID NO:3) is preferred. Another preferred variant tat peptide consists of GRKKRRQRRR (SEQ ID NO:1). Other tat peptides that can be used include GRK-KRRQRRRPQ (SEQ ID NO:4) and GRKKRRQRRRP (SEQ ID NO:72). Other tat peptides comprises at least eight contiguous amino acids of the sequence GRKKRRQRRR. Other tat peptides that facilitate uptake of a pharmacological agent without inhibiting N-type calcium channels include those presented in Table 3. Another preferred tat peptide is referred to as rv-tat or RRRQRRKKRGY (amino acids 1-11 of SEQ ID NO:70).

TABLE 3

| | |
|---|---|
| X-FGRKKRRQRRR (F-Tat) | (SEQ ID NO: 3) |
| X-GKKKKKQKKK | (SEQ ID NO: 50) |
| X-RKKRRQRRR | (SEQ ID NO: 51) |
| X-GAKKRRQRRR | (SEQ ID NO: 52) |
| X-AKKRRQRRR | (SEQ ID NO: 53) |
| X-GRKARRQRRR | (SEQ ID NO: 54) |
| X-RKARRQRRR | (SEQ ID NO: 55) |
| X-GRKKARQRRR | (SEQ ID NO: 56) |
| X-RKKARQRRR | (SEQ ID NO: 57) |
| X-GRKKRRQARR | (SEQ ID NO: 58) |
| X-RKKRRQARR | (SEQ ID NO: 59) |
| X-GRKKRRQRAR | (SEQ ID NO: 60) |
| X-RKKRRQRAR | (SEQ ID NO: 61) |
| X-RRPRRPRRPRR | (SEQ ID NO: 62) |
| X-RRARRARRARR | (SEQ ID NO: 63) |
| X-RRARRRARR | (SEQ ID NO: 64) |
| X-RRRPRRRPRR | (SEQ ID NO: 65) |
| X-RRPRRPRR | (SEQ ID NO: 66) |
| X-RRARRARR | (SEQ ID NO: 67) |

X can represent a free amino terminus, one or more amino acids, or a conjugated moiety. Internalization peptides can be used in inverso or retro or inverso retro form with or without the linked peptide or peptidomimetic being in such form.

Internalization peptides can be attached to pharmacological agents by conventional methods. For example, the agents can be joined to internalization peptides by chemical linkage, for instance via a coupling or conjugating agent. Numerous such agents are commercially available and are reviewed by Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene)bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

IV. Inflammatory Response to Internalization Peptides

The present inventors have found that internalization peptides such as tat have capacity to induce an inflammatory response on administration to a subject. The inflammatory response is usually detectable within 1, 5, 10, 20, 30, or 60 min of administering the peptide, but typically disappears within 24 hr of administration of the peptide (assuming the peptide is not readministered). The inflammatory response is dose-dependent. The inflammatory response typically recurs at similar intensity on readministering the peptide. One aspect of the inflammatory response is often a transient decrease in blood pressure occurring within a period of about 0-30 min after administering the internalization peptide.

The inflammatory response is characterized by a degranulation of mast cells and consequent release of histamine and other mediators of inflammation, such as chemokines, cytokines, leukotrienes, lipases, proteases, kinins, cytokines, arachidonic acid derivatives such as prostaglandins, interleukins, and/or nitric oxide (see FIG. 12). The histamine and/or other released mediators of inflammation give rise to a number of symptoms of inflammation including redness of the skin, heat, swelling, hypotension and/or reduced pulse. Histamine release can also result in vasodilation, hypotension, bronchoconstriction, smooth muscle activation, separation of endothelial cells (responsible for hives), pain, itching, increased capillary permeability, glandular hypersecretion, smooth muscle spasm, and/or tissue infiltration of inflammatory cells, as well as gastric acid secretion, and decreased release of neurotransmitters such as histamine, acetylcholine, norepinephrine, and serotonin. Detection of any of these sequelae, particularly easily measurable ones, such as hypotension or a skin rash, such as hives, can be used as an indicator of mast cell degranulation.

V. Anti-Inflammatory Agents

A wide variety of anti-inflammatory agents are readily available to inhibit one or more aspects of the type of inflammatory response noted above (see, e.g., U.S. Pat. No. 6,204,245, incorporated by reference).

A preferred class of anti-inflammatory agent is mast cell degranulation inhibitors. This class of compounds includes cromolyn (5,5'-(2-hydroxypropane-1,3-diyl)bis(oxy)bis(4-oxo-4H-chromene-2-carboxylic acid) (also known as cromoglycate), and 2-carboxylatochromon-5'-yl-2-hydroxypropane derivatives such as bis(acetoxymethyl), disodium cromoglycate, nedocromil (9-ethyl-4,6-dioxo-10-propyl-6,9-dihydro-4H-pyrano[3,2-g]quinoline-2,8-dicarboxylic acid) and tranilast (2-{[(2E)-3-(3,4-dimethoxyphenyl)prop-2-enoyl]amino}), and lodoxamide (2-[2-chloro-5-cyano-3-(oxaloamino)anilino]-2-oxoacetic acid). Reference to a specific compound includes pharmaceutically acceptable salts of the compound Cromolyn is readily available in formulations for nasal, oral, inhaled or intravenous administration. Although practice of the invention is not dependent on an understanding of mechanism, it is believed that these agents act at an early stage of inflammatory response induced by an internalization peptide and are thus most effective at inhibiting development of its sequelae including a transient reduction in blood pressure. Other classes of anti-inflammatory agent discussed below serve to inhibit one or more downstream events resulting from mast cell degranulation, such as inhibiting histamine from binding to an H1 or H2 receptor, but may not inhibit all sequelae of mast cell degranulation or may require higher dosages or use in combinations to do so. Table 8 below summarizes the names, chemical formulate and FDA status of several mast cell degranulation inhibitors that can be used with the invention.

TABLE 8

| Drug Name | Alternative Names | Chemical Formula | FDA status |
|---|---|---|---|
| Azelastine | Astelin, Optivar | 4-[(4-chlorophenyl)methyl]-2-(1-methylazepan-4-yl)phthalazin-1-one | Approved |
| Bepotastine | Bepotastine besilate, Betotastine besilate, TAU-284DS, bepotastine | 4-[4-[(4-chlorophenyl)-pyridin-2-ylmethoxy]piperidin-1-yl]butanoic acid | Approved |
| Chlorzoxazone | Biomioran, EZE-DS, Escoflex, Flexazone, Mioran, Miotran, Myoflexin, Myoflexine, Neoflex, Paraflex, Parafon Forte Dsc, Pathorysin, Relaxazone, Remular, Remular-S, Solaxin, Strifon Forte Dsc, Usaf Ma-10 | 5-chloro-3H-1,3-benzoxazol-2-one | Approved |
| Cromolyn | Cromoglycate, Chromoglicate, Chromoglicic Acid, Aarane, Alercom, Alerion, Allergocrom, ApoCromolyn, Children't Nasalcrom, Colimune, Crolom, Cromolyn Nasal Solution, Cromoptic, Cromovet, Fivent, Gastrocrom, Gastrofrenal, GenCromoglycate, Inostral, Intal, Intal, Inhaler, Intal, Syncroner, Introl, Irtan, Lomudal, Lomupren, Lomusol, Lomuspray, Nalcrom, Nalcron, Nasalcrom, Nasmil, Opticrom, Opticron, Rynacrom, Sofro, Vistacrom, Vividrin | 5-[3-(2-carboxy-4-oxochromen-6-yl)oxy-2-hydroxypropoxy]-4-oxochromene-2-carboxylic acid | Approved |
| Epinastine | Elestat | C16H15N3, CAS 80012-43-7 | Approved |
| Isoproterenol | Aerolone, Aleudrin, Aleudrine, Aludrin, Aludrine, Asiprenol, Asmalar, Assiprenol, Bellasthman, Bronkephrine, Euspiran, Isadrine, Isonorene, Isonorin, Isorenin, Isuprel, Isuprel Mistometer, Isupren, Medihaler-Iso, NeoEpinine, Neodrenal, Norisodrine, m Norisodrine, Aerotrol, Novodrin, Proternol, Respifral, Saventrine, Vapo-Iso | 4-[1-hydroxy-2-(propan-2-ylamino)ethyl]benzene-1,2-diol | Approved |
| Ketotifen | Zaditor | C19H19NOS, CAS 34580-14-8 | Approved |
| Lodoxamide (lodoxamide tromethamine) | Alomide | N,N'-(2-chloro-5-cyano-m-phenylene)dioxamic acid tromethamine salt | Approved |
| Nedocromil | Alocril, Nedocromil [USAN:BAN:INN], Tilade | 9-ethyl-4,6-dioxo-10-propylpyrano[5,6-g]quinoline-2,8-dicarboxylic acid | Approved |
| Olopatadine | Olopatadine Hydrochloride Patanol | 2-[(11Z)-11-(3-dimethylaminopropylidene)-6H-benzo[c][2]benzoxepin-2-yl]acetic acid | Approved |
| Pemirolast | Alamast | 9-methyl-3-(2H-tetrazol-5-yl)pyrido[2,1-b]pyrimidin-4-one | Approved |
| Pirbuterol | Maxair | 6-[2-(tert-butylamino)-1-hydroxyethyl]-2-(hydroxymethyl)pyridin-3-ol | Approved |

Another class of anti-inflammatory agent is anti-histamine compounds. Such agents inhibit the interaction of histamine with its receptors thereby inhibiting the resulting sequelae of inflammation noted above. Many anti-histamines are commercially available, some over the counter. Examples of anti-histamines are azatadine, azelastine, burfroline, cetirizine, cyproheptadine, doxantrozole, etodroxizine, forskolin, hydroxyzine, ketotifen, oxatomide, pizotifen, proxicromil, N,N'-substituted piperazines or terfenadine. Anti-histamines vary in their capacity to block anti-histamine in the CNS as well as peripheral receptors, with second and third generation anti-histamines having selectivity for peripheral receptors. Acrivastine, Astemizole, Cetirizine, Loratadine, Mizolastine, Levocetirizine, Desloratadine, and Fexofenadine are examples of second and third generation anti-histamines. Anti-histamines are widely available in oral and topical formulations. Some other anti-histamines that can be used are summarized in Table 9 below.

Cortisone, Hydrocortisone (Cortef), Prednisone (Deltasone, Meticorten, Orasone), Prednisolone (Delta-Cortef, Pediapred, Prelone), Triamcinolone (Aristocort, Kenacort), Methylprednisolone (Medrol), Dexamethasone (Decadron, Dexone, Hexadrol), and Betamethasone (Celestone). Corticosteriods are widely available in oral, intravenous and topical formulations.

Nonsteroidal anti-inflammatory drugs (NSAIDs) can also be used. Such drugs include aspirin compounds (acetylsalicylates), non-aspirin salicylates, diclofenac, diflunisal, etodolac, fenoprofen, flurbiprofen, ibuprofen, indomethacin, ketoprofen, meclofenamate, naproxen, naproxen sodium, phenylbutazone, sulindac, and tometin. However, the anti-inflammatory effects of such drugs are less effective than those of anti-histamines or corticosteroids.

Stronger anti-inflammatory drugs such as azathioprine, cyclophosphamide, leukeran, and cyclosporine can also be used but are not preferred because they are slower acting and/or associated with side effects. Biologic anti-inflamma-

TABLE 9

| Drug Name | Alternative Names | Chemical Formula | FDA status |
|---|---|---|---|
| Ketotifen fumarate | Ketotifen, Zaditor | C19H19NOS | Approved |
| Mequitazine | Butix, Instotal, Kitazemin, Metaplexan, Mircol, Primalan, Vigigan, Virginan, Zesulan | 10-(1-azabicyclo[2.2.2]octan-8-ylmethyl)phenothiazine | Approved |
| Dexbrompheniramine | Ilvan | (3S)-3-(4-bromophenyl)-N,N-dimethyl-3-pyridin-2-ylpropan-1-amine | Approved |
| Methdilazine | Bristaline, Dilosyn, Disyncram, Disyncran, Tacaryl, Tacaryl hydrochloride, Tacazyl, Tacryl | 10-[(1-methylpyrrolidin-3-yl)methyl]phenothiazine | Approved |
| Chlorpheniramine | Aller-Chlor, Allergican, Allergisan, Antagonate, Chlo-Amine, Chlor-Trimeton, Chlor-Trimeton Allergy, Chlor-Trimeton Repetabs, Chlor-Tripolon, Chlorate, Chloropiril, Cloropiril, Efidac 24 Chlorpheniramine Maleate, Gen-Allerate, Haynon, Histadur, Kloromin, Mylaramine, Novo-Pheniram, Pediacare Allergy Formula, Phenetron, Piriton, Polaramine, Polaronil, Pyridamal 100, Telachlor, Teldrin | 3-(4-chlorophenyl)-N,N-dimethyl-3-pyridin-2-ylpropan-1-amine | Approved |
| Brompheniramine | Bromfed, Bromfenex, Dimetane, Veltane | 3-(4-bromophenyl)-N,N-dimethyl-3-pyridin-2-ylpropan-1-amine | Approved |
| Terbutaline | Brethaire, Brethine, Brican, Bricanyl, Bricar, Bricaril, Bricyn | 5-[2-(tert-butylamino)-1-hydroxyethyl]benzene-1,3-diol | Approved |
| pimecrolimus | Elidel | (3S,4R,5S,8R,9E,12S,14S,15R,16S,18R,19R,26aS)-3-{(E)-2-[(1R,3R,4S)-4-Chloro-3-methoxycyclohexyl]-1-methylvinyl}-8-ethyl-5,6,8,11,12,13,14,15,16,17,18,19,24,25,26,26a-hexadecahydro-5,19-dihydroxy-14,16-dimethoxy-4,10,12,18-tetramethyl-15,19-epoxy-3H-pyrido[2,1-c][1,4]oxaazacyclotricosine-1,7,20,21(4H,23H)-tetrone | Approved as topical, Investigational as oral |

Another class of anti-inflammatory agent useful in inhibiting the inflammatory response is corticosteroids. These compounds are transcriptional regulators and are powerful inhibitors of the inflammatory symptoms set in motion by release of histamine and other compounds resulting from mast cell degranulation. Examples of corticosteroids are tory agents, such as Tysabri® or Humira®, can also be used but are not preferred for the same reasons.

Different classes of drugs can be used in combinations in inhibiting an inflammatory response. A preferred combination is a mast cell degranulation inhibitor and an anti-histamine.

VI. Conjugation

The inflammatory response inducible by an internalization peptide can alternatively (or additionally) be reduced by linking the internalization peptide to biotin or similar molecule to form a conjugate. The conjugate retains an ability to facilitate uptake of a linked pharmacologic agent into cells into cells but induces a reduced inflammatory response compared to the same internalization peptide without the biotin. Conjugated internalization peptides can be screened to confirm desired uptake and lack of (or decrease in) a resulting immune response.

Alternatives to biotin that can be used to form conjugates of an internalization peptide include acetyl, benzoyl, alkyl group (aliphatic), pyroglutamate, alkyl group with cycloalkyl group at the end, biotin with alkyl spacer, (5,6)-FAM. The biotin or other molecule can be linked to the internationalization peptide through an amide chemistry, sulphamide chemistry, sulphone chemistry, and/or alkylation chemistry.

VII. Patients Amenable to Treatment/Prophylaxis

A broad range of patients are amenable to treatment by the methods of invention as exemplified by the pharmacologic agents and associated conditions listed in Table 1. The methods are of particular use in such patients having a condition that would exacerbate any inflammation resulting from an internalization peptide, for example, a patient suffering from hypertension, elevated pulse or other signs or symptoms of inflammation. The methods are also particularly useful in methods of treatment requiring a high dose of pharmacological agent linked to internalization peptide. Strictly it is the dose of the internalization peptide rather than the linked pharmacological agent that determines presence and extent of the inflammatory response, if any. However, the does of internalization peptide is of course determined by the dose of the linked pharmacological agent. For example, an inflammatory response may become noticeable at a dose of greater than 1.5 mg/kg internalization peptide). In treatment of some diseases, the effective dose of pharmacologic agent and consequently linked internalization peptide is too low to induce an inflammatory response in most patients. Nevertheless, the sensitivity of individual patients to an inflammatory response can vary, and treatment with a mild anti-inflammatory agent, such as a histamine, can still be a worthwhile precaution.

One class of patients of particular interest is those having or at risk of a disease or condition characterized by excitotoxicity. Such diseases and conditions include stroke, epilepsy, hypoxia, traumatic injury to the CNS not associated with stroke such as traumatic brain injury and spinal cord injury, Alzheimer's disease and Parkinson's disease. Such conditions also include patients undergoing surgery that affects or may affect a vessel (e.g., jugular vein or carotid artery) supplying or removing blood to or from the brain, particularly patients undergoing neurosurgery, such as endovascular surgery to repair an aneurysm or endovascular surgery to a blood vessel supplying a limb, spinal cord, retina or kidney (see 61/185,989 filed Jun. 10, 2009 and attorney docket 026373-00920PC filed herewith). Such repair can be effected for example by inserting a stent or coil into the blood vessel subject to the aneurysm The methods of the invention are suitable for treating both male and female patients having or at risk of such diseases and conditions.

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

TABLE 4

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf.

The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac or pulmonary surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop.

However, the obstruction (blood clot) occurs for a short time and tends to resolve itself through normal mechanisms. Patients undergoing heart, pulmonary or neuro-surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

VIII. Delivery of Pharmacological Agent with an Anti-Inflammatory Agent

In methods in which a pharmacological agent linked to an internalization peptide is administered with an anti-inflammatory agent, the two entities are administered sufficiently proximal in time that the anti-inflammatory agent can inhibit an inflammatory response inducible by the internalization peptide. The anti-inflammatory agent can be administered before, at the same time as or after the pharmacologic agent, but is preferably administered before. The preferred time depends in part on the pharmacokinetics and pharmacodynamics of the anti-inflammatory agent. The anti-inflammatory agent can be administered at an interval before the pharmacologic agent such that the anti-inflammatory agent is near maximum serum concentration at the time the pharmacologic agent is administered. Typically, the anti-inflammatory agent is administered between 6 hours before the pharmacological agent and one hour after. For example, the anti-inflammatory agent can be administered between 1 hour before and 30 min after the pharmacological agent. Preferably the anti-inflammatory agent is administered between 30 minutes before and 15 minutes after the pharmacological agent, and more preferably within 15 minutes before and the same time as the pharmacological agent. In some methods, the anti-inflammatory agent is administered before the pharmacological agent within a period of 15, 10 or 5 minutes before the pharmacological agent is administered. In some methods, the agent is administered 1-15, 1-10 or 1-5 minutes before the pharmacological agent.

When administration of an agent is not instantaneous, such as with intravenous infusion, the anti-inflammatory agent and pharmacological agent are considered to be administered at the same time if their periods of administration are co-extensive or overlap. Time periods of administration before administration start from the beginning of its administration. Time periods after administration start from the end of its administration. Time periods referring to the administration of the anti-inflammatory agent refer to the beginning of its administration.

When an anti-inflammatory agent is said to be able to inhibit the inflammatory response of a pharmacological agent linked to an internalization peptide what is meant is that the two are administered sufficiently proximate in time that the anti-inflammatory agent would inhibit an inflammatory response inducible by the pharmacological agent linked to the internalization peptide if such a response occurs in a particular patient, and does not necessarily imply that such a response occurs in that patient. Some patients are treated with a dose of pharmacological agent linked to an internalization peptide that is associated with an inflammatory response in a statistically significant number of patients in a controlled clinical or nonclinical trial. It can reasonably be assumed that a significant proportion of such patients although not necessarily all develop an anti-inflammatory response to the pharmacological agent linked to the internalization peptide. In some patients, signs or symptoms of an inflammatory response to the pharmacological agent linked to the internalization peptide are detected or detectable.

In clinical treatment of an individual patient, it is not usually possible to compare the inflammatory response from a pharmacological agent linked to an internalization peptide in the presence and absence of an anti-inflammatory agent. However, it can reasonably be concluded that the anti-inflammatory agent inhibits an anti-inflammatory response inducible by the peptide if significant inhibition is seen under the same or similar conditions of co-administration in a controlled clinical or pre-clinical trial. The results in the patient (e.g., blood pressure, heart rate, hives) can also be compared with the typical results of a control group in a clinical trial as an indicator of whether inhibition occurred in the individual patient. Usually, the anti-inflammatory agent is present at a detectable serum concentration at some point within the time period of one hour after administration of the pharmacologic agent. The pharmacokinetics of many anti-inflammatory agents is widely known and the relative timing of administration of the anti-inflammatory agent can be adjusted accordingly. The anti-inflammatory agent is usually administered peripherally, i.e., segregated by the blood brain barrier from the brain. For example, the anti-inflammatory agent can be administered orally, nasally, intravenously or topically depending on the agent in question. If the anti-inflammatory agent is administered at the same time as the pharmacologic agent, the two can be administered as a combined formulation or separately.

In some methods, the anti-inflammatory agent is one that does not cross the blood brain barrier when administered orally or intravenously at least in sufficient amounts to exert a detectable pharmacological activity in the brain. Such an agent can inhibit mast cell degranulation and its sequelae resulting from administration of the pharmacological agent in the periphery without itself exerting any detectable therapeutic effects in the brain. In some methods, the anti-inflammatory agent is administered without any co-treatment to increase permeability of the blood brain barrier or to derivatize or formulate the anti-inflammatory agent so as to increase its ability to cross the blood brain barrier. However, in other methods, the anti-inflammatory agent, by its nature, derivatization, formulation or route of administration, may by entering the brain or otherwise influencing inflammation in the brain, exert a dual effect in suppressing mast-cell degranulation and/or its sequelae in the periphery due to an internalization peptide and inhibiting inflammation in the brain. Strbian et al., WO 04/071531 have reported that a mast cell degranulation inhibitor, cromoglycate, administered i.c.v. but not intravenously has direct activity in inhibiting infarctions in an animal model.

In some methods, the patient is not also treated with the same anti-inflammatory agent co-administered with the pharmacological agent in the day, week or month preceding and/or following co-administration with pharmacological agent. In some methods, if the patient is otherwise being treated with the same anti-inflammatory agent co-administered with the pharmacological agent in a recurring regime (e.g., same amount, route of delivery, frequency of dosing, timing of day of dosing), the co-administration of the anti-inflammatory agent with the pharmacological agent does not comport with the recurring regime in any or all of amount, route of delivery, frequency of dosing or time of day of dosing. In some methods, the patient is not known to be suffering from an inflammatory disease or condition requiring administration of the anti-inflammatory agent co-administered with the pharmacological agent in the present methods. In some methods, the patient is not suffering from asthma or allergic disease treatable with a mast cell degranulation inhibitor. In some methods, the anti-inflammatory agent and pharmacological agent are each administered once and only once within a window as defined above, per episode of disease, an episode being a relatively short period in which symptoms of disease are present flanked by longer periods in which symptoms are absent or reduced.

The anti-inflammatory agent is administered in a regime of an amount, frequency and route effective to inhibit an inflammatory response to an internalization peptide under conditions in which such an inflammatory response is known to occur in the absence of the anti-inflammatory. An inflammatory response is inhibited if there is any reduction in signs or symptoms of inflammation as a result of the anti-inflammatory agent. Symptoms of the inflammatory response can include redness, rash such as hives, heat, swelling, pain, tingling sensation, itchiness, nausea, rash, dry mouth, numbness, airway congestion. The inflammatory response can also be monitored by measuring signs such as blood pressure, or heart rate. Alternatively, the inflammatory response can be assessed by measuring plasma concentration of histamine or other compounds released by mast cell degranulation. The presence of elevated levels of histamine or other compounds released by mast cell degranulation, reduced blood pressure, skin rash such as hives, or reduced heart rate are indicators of mass cell degranulation. As a practical matter, the doses, regimes and routes of administration of most of the anti-inflammatory agents discussed above are available in the Physicians' Desk Reference and/or from the manufacturers, and such anti-inflammatories can be used in the present methods consistent with such general guidance.

IX. Methods of Treatment/Prophylaxis a) Methods of Treatment

A chimeric agent comprising a pharmacologic agent attached to an internalization peptide is administered in an amount, frequency and route of administration effective to cure, reduce or inhibit further deterioration of at least one sign or symptom of a disease in a patient having the disease being treated. A therapeutically effective amount means an amount of chimeric agent sufficient significantly to cure, reduce or inhibit further deterioration of at least one sign or symptom of the disease or condition to be treated in a population of patients (or animal models) suffering from the disease treated with a chimeric agent of the invention relative to the damage in a control population of patients (or animal models) suffering from that disease or condition who are not treated with a chimeric agent of the invention. The amount is also considered therapeutically effective if an individual treated patient achieves an outcome more favorable than the mean outcome in a control population of comparable patients not treated by methods of the invention. A therapeutically effective regime involves the administration of a therapeutically effective dose at a frequency and route of administration needed to achieve the intended purpose.

For a patient suffering from stroke or other ischemic condition, the chimeric agent is administered in a regime comprising an amount frequency and route of administration effective to reduce the damaging effects of stroke or other ischemic condition. When the condition requiring treatment is stroke, the outcome can be determined by infarction volume or disability index, and a dosage is considered therapeutically effective if an individual treated patient shows a disability of two or less on the Rankin scale and 75 or more on the Barthel scale, or if a population of treated patients shows a significantly improved (i.e., less disability) distribution of scores on a disability scale than a comparable untreated population, see Lees et at 1., N Engl J Med 2006; 354:588-600. A single dose of chimeric agent is usually sufficient for treatment of stroke.

b) Methods of Prophylaxis

The invention also provides methods and compositions for the prophylaxis of a disorder in a subject at risk of that disorder. Usually such a subject has an increased likelihood of developing the disorder (e.g., a condition, illness, disorder or disease) relative to a control population. The control population for instance can comprise one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of transient cerebral ischemic attack because the frequency of transient cerebral ischemic attack is increased in a population of subjects who have undergone heart surgery as compared to a population of subjects who have not.

Other common risk factors for stroke include age, family history, gender, prior incidence of stroke, transient ischemic attack or heart attack, high blood pressure, smoking, diabetes, carotid or other artery disease, atrial fibrillation, other heart diseases such as heart disease, heart failure, dilated cardiomyopathy, heart valve disease and/or congenital heart defects; high blood cholesterol, and diets high in saturated fat, trans fat or cholesterol.

Pharmacological agents linked to an internalization peptide are administered to patients at risk of a disease but not yet having the disease in an amount, frequency and route sufficient to prevent, delay or inhibit development of at least one sign or symptom of the disease. A prophylactically effective amount means an amount of chimeric agent sufficient significantly to prevent, inhibit or delay at least one sign or symptom of the disease in a population of patients (or animal models) at risk of the disease relative treated with the agent compared to a control population of patients (or animal models) at risk of the disease not treated with a chimeric agent of the invention. The amount is also considered prophylactically effective if an individual treated patient achieves an outcome more favorable than the mean outcome in a control population of comparable patients not treated by methods of the invention. A prophylactically effective regime involves the administration of a prophylactically effective dose at a frequency and route of administration needed to achieve the intended purpose. For prophylaxis of stroke in a patient at imminent risk of stroke (e.g., a patient undergoing heart surgery), a single dose of chimeric agent is usually sufficient.

X. Pharmaceutical Compositions, Dosages, and Routes of Administration

The chimeric agents of the invention can be administered in the form of a pharmaceutical composition. Pharmaceutical compositions are typically manufactured under GMP conditions. Pharmaceutical compositions can be provided in unit dosage form (i.e., the dosage for a single administration). Pharmaceutical compositions can be manufactured by means of conventional mixing, dissolving, granulating, dragee-making, levigating, emulsifying, encapsulating, entrapping or lyophilizing processes. For example, lyophilized chimeric agents of the invention can be used in the formulations and compositions described below.

Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

Some pharmaceutical composition are a co-formulation of an active agent and an anti-inflammatory agent as described above for simultaneous administration of the active agent and anti-inflammatory agent. Such co-formulations typically have the active agents dissolved in solution, although the active agents can also by co-lyophilized or individually lyophilized and mixed, and then reformulated before use. Whether mixed from solutions or by reconstituting a lyophilysate, the formulation is preferably substantially free of visible particles on formation (i.e., less than 10%, 5% or 1% of each active agent is in particulate form). The formulation preferably remains substantially free of visible particles on storage for at least a week, a month or a year. The formulation can be stored in cold liquid form (in a refrigerator at about 4 degrees C. or can be stored in frozen form.

One example of such a composition is a co-formulation of Tat-NR2B9c with lodoxamide. The two active agents can be formulated in an aqueous solution at a range of concentrations of the active agents. For example, the concentration of Tat-NR2B9c can range from about 1-30 mg/ml and that of lodoxamide from 0.1 to 5 mg/ml. The co-formulation can also contain a tonicity agent (e.g., NaCl), hydrochloric acid or sodium hydroxide to adjust pH, a buffer a preservative, and various other excipients used in the commercial preparation of lodoxamide, such as mannitol, hydroxypropyl methylcellulose 2910, sodium citrate, citric acid, edetate disodium, tyloxapol. The formulation can be prepared, for example, simply by mixing Tat-NR2B9c in saline with Alomide (lodoxamide), as further defined in the Examples and vortexing. The Tat-NR2B9c is preferably at a concentration of 10-30 mg/ml or more preferably 20 mg/ml. The NA-1 and lodoxamide are combined in a ratio of about 2:3 or more preferably 1.89:3.11

Administration can be parenteral, intravenous, oral, subcutaneous, intra-arterial, intracranial, intrathecal, intraperitoneal, topical, intranasal or intramuscular. Intravenous administration is preferred.

Pharmaceutical compositions for parenteral administration are preferably sterile and substantially isotonic. For injection, chimeric agents can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively the chimeric agents can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the chimeric agents can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the chimeric agents can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver chimeric agents. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the chimeric agents for a few weeks up to over 100 days. Depending on the chemical nature and the biological stability of the therapeutic reagent, additional strategies for protein stabilization can be employed.

As the chimeric agents of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

Chimeric agents comprising an internalization peptide linked to a pharmacologic agent can be used at the same or lower dosage on a molar basis as the pharmacologic agent alone, and can be administered by the same route as the pharmacologic agent alone, and for treatment of the same disease(s) as the pharmacologic agent alone.

For treatment of stroke, preferred dosage ranges include 0.001 to 20 μmol chimeric peptide or peptidomimetic per kg patient body weight, optionally 0.03 to 3 μmol chimeric peptide per kg patient body weight. In some methods, 0.1-20 μmol chimeric peptide or peptidomimetic per kg patient body weight is administered. In some methods, 0.1-10 μmol chimeric peptide or peptidomimetic per kg patient body weight, more preferably about 0.3 μmol chimeric peptide per kg patient body weight. In other instances, the dosages range is from 0.005 to 0.5 μmol chimeric peptide or peptidomimetic per kg patient body weight. Dosage per kg body weight can be converted from rats to humans by dividing by 6.2 to compensate for different surface area to mass ratios. Dosages can be converted from units of moles to grams by multiplying by the molar weight of a chimeric peptide or peptidomimetic. Suitable dosages of chimeric peptides or peptidomimetics for use in humans can include 0.001 to 5 mg/kg patient body weight, or 0.005 to 1 mg/kg patient body weight or 0.05 to 1 mg/kg, or 0.09 to 0.9 mg/kg. In absolute weight for a 75 kg patient, these dosages translate to 0.075-375 mg, 0.375 to 75 mg or 3.75 mg to 75 mg or 6.7 to 67 mg. Rounded to encompass variations in e.g., patient weight, the dosage is usually within 0.05 to 500 mg, preferably 0.1 to 100 mg, 0.5 to 50 mg, or 1-20 mg. Indicated dosages should be understood as including the margin of error inherent in the accuracy with which dosages can be measured in a typical hospital setting.

The co-administration of an anti-inflammatory agent with a pharmacological agent is particularly useful when the pharmacological agent is administered at higher doses when mast cell degranulation is most likely to ensue. For administration of the chimeric agent Tat-NR2B9c to humans, an approximate dosage level when mast cell degranulation is likely to occur is a dose of greater than or equal to 2.6 mg/mg. Thus, co-administration of an anti-inflammatory agent is particularly useful at a dose of Tat-NR2B9c of greater than or equal to 2.6 mg/kg, 3 mg/kg, 5 mg/kg or 10 mg/kg. Usually the dosage is not higher than 50 mg/kg.

Although lower dosages may be equally effective in many patients, use of high dosages is advantageous in extremely acute diseases, such as stroke, in which if the first administration of a pharmacological agent is insufficient, there may be little opportunity for a second. Of course, some variation is expected between individual patients in the precise dosage at which onset of mast cell degranulation occurs. Therefore, it can also be useful to administer the anti-inflammatory as a precaution at lower dosages of Tat-NR2B9c in case mast cell degranulation occurs in a few patients with greater than normal susceptibility. For example, the anti-inflammatory agent can be administered at dosages of Tat-NR2B9c of greater or equal to 0.5 mg/kg, 1 mg/mg or 2 mg/kg.

In some methods, in which a population of patients are treated, some patients are administered an anti-inflammatory agent and some are not depending on the dose of the pharmacological agent linked to the internalization peptide with patients receiving a higher dose receiving the anti-inflammatory agent. The transition point for administering or not administering the anti-inflammatory agent for Tat-NR2B9c can be a dose from about 1-3 mg/kg. For example, patients receiving 1 mg/kg or less are not administered the anti-inflammatory agent, patients receiving 3 mg/kg or greater are administered the anti-inflammatory agent and patients receiving a dose of greater than 1 and less than 3 mg/kg, may or may not be administered the anti-inflammatory. Of course, the above scheme is just an example, and a different transition point can be set. Also, all patients receiving a dose at or above the transition point can be administered the anti-inflammatory and all patients receiving a dose below the transition point may be treated without the anti-inflammatory. Also, all patients can be administered the anti-inflammatory without regard to the dose of the pharmacological agent linked to the internalization peptide, as discussed above. The dosages indicated above for the chimeric agent Tat-NR2B9c (YGRKKRRQRRRKLSSIESDV; SEQ ID NO:6) can also be used for close variants of that agent in which one or a few amino acids are substituted, inserted or deleted and the molecular weight remains the same within about +/−25% However, in general, equivalent dosages of other agents for purposes of determining when to administer an inflammatory agent can be determined by calculating the dose of that agent that delivers an equimolar amount of internalization peptide to a given dose of Tat-NR2B9c.

The amount of chimeric agent administered depends on the subject being treated, on the subject's weight, the severity of the affliction, the manner of administration and the judgment of the prescribing physician. The therapy can be repeated intermittently while symptoms are detectable or even when they are not detectable. The therapy can be provided alone or in combination with other drugs. For treatment of stroke, the dose of pharmacologic agent linked to an internalization peptide is usually administered within 24 hours of onset of stroke, preferably within 6 hours of onset of stroke.

XI. Kits

Kits are provided for carrying out the present methods. The kits include one or more pharmacologic agents of interest, attached to an internalization peptide. The internalization peptide can be biotinylated, and/or the kit can contain an anti-inflammatory agent. The instant kit optionally contains means for administering the pharmacologic agents and/or anti-inflammatory agent. The kit can also include one or more buffers, additives, fillers or diluents. The kit can also provide one or more printed instructions on the administration and dosage regimen to be followed.

XII. Screening Methods

A. Measuring Internalization Activity

Variants of the tat or other internalization peptide can be tested for transport activity in an animal. Internalization peptides can be tested alone or when linked to an active agent, such an active peptide, e.g., KLSSIESDV (SEQ ID NO:5). The internalization peptide, optionally linked to an active agent, such as a peptide, is labeled, preferably with a fluorescent label, such as dansyl chloride. The internalization peptide is then injected peripherally into an animal, such as a mouse. Intraperitoneal or intravenous injection is suitable, for example. About an hour after injection, the mice are sacrificed, perfused with fixative solution (3% paraformaldehyde, 0.25% glutaraldehyde, 10% sucrose, 10 U/mL heparin in saline). Brains are then removed, frozen and sections. Sections are analyzed for fluorescence using a confocal microscope. Internalization activity is determined from fluorescence, optionally relative to positive and negative controls. A suitable positive control is the standard tat peptide linked to the same active peptide (if present) as the internalization peptide under test. A suitable negative control is fluorescently labeled active peptide not linked to an internalization peptide. Unlabelled vehicle can also be used as a negative control.

Similar experiments can be performed in cell culture to test variants of tat or other internalization peptide (see US20030050243). A variant fluorescently labeled tat peptide, optionally linked to an active peptide is applied to a cortical neuronal culture. Uptake is determined using fluorescence microscopy over several minutes after application. Increased uptake can be determined relative to positive and negative controls as described for the experiments on uptake in an animal.

2. Measuring Activity in Treating Stroke

The activity of chimeric agents comprising a internalization peptide linked to an agent can be tested in various animal models of stroke. In one such model, in adult male Sprague-Dawley rats subjected to transient middle cerebral artery occlusion (MCAO) for 90 minutes by the intraluminal suture method (36,37). Animals are fasted overnight and injected with atropine sulfate (0.5 mg/kg IP). After 10 minutes anesthesia is induced. Rats are orally intubated, mechanically ventilated, and paralyzed with pancuronium bromide (0.6 mg/kg IV). Body temperature is maintained at 36.5-37.5° C., with a heating lamp. Polyethylene catheters in the femoral artery and vein are used to continuously record blood pressure and to sample blood for gas and pH measurements. Transient MCAO is achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Animals are treated with either a chimeric agent under test or a negative or positive control. Treatment can be either before or up to one hour after inducing ischemia. A negative control can be vehicle. A positive control can be the Tat-NR2B9c peptide, YGRKKRRQRRRKLSSIESDV (SEQ ID NO:6), previously shown to be effective. The chimeric agent is delivered by a single intravenous bolus injection 45 min prior to MCAO (3 nmoles/g). After administering compounds to the animals, infarction volume and/or disability index are determined. Infarction volumes are usually determined 24 hr post treatment but can be determined at a later time such as 3, 7, 14 or 60 days. Disability index can be monitored over time, e.g., at 2 hr post treatment, 24 hr post treatment, one week and one month post treatment. Chimeric agents showing a statistically significant reduction in infarction volume and/or disability index relative to control animals not treated with the compounds are identified as having activity useful for practicing the methods of the invention.

Similar experiments can be performed in animal subject to permanent ischemia. Permanent ischemia of the middle cerebral artery pial vessel can be carried out as described by Forder et al., Am J Physiol Heart Circ Physiol 288:H1989-H1996 (2005). In brief, the right ECA is cannulated with PE 10 polyethylene tubing. The skull is exposed via a midline incision, and a 6- to 8-mm cranial window is made over the right somatosensory cortex (2 mm caudal and 5 mm lateral to bregma). The pial arteries are visualized by injecting small boluses (10-20 µL) of the vital dye patent blue violet (10 mMol/L; Sigma) in normal saline, into the ECA. The same three pial arteriolar MCA branches are electrically cauterized and dye injections are repeated to ensure the interruption of flow through the cauterized arterioles. The incision is then closed and the animal returned to its cage and allowed free access to food and water. This permanent ischemia model produces a highly reproducible small infarction limited to the cortex underlying the coagulated terminal pial arteries.

The left middle cerebral artery can be occluded by the intraluminal suture method described by Longa, Stroke 20, 84-91 (1989). In brief, the left common carotid artery (CCA) is exposed through a midline neck incision and is dissected free from surrounding nerves and fascia, from its bifurcation to the base of the skull. The occipital artery branches of the external carotid artery (ECA) are then isolated, and these branches dissected and coagulated. The ECA is dissected further distally and coagulated along with the terminal lingual and maxillary artery branches, which are then divided. The internal carotid artery (ICA) is isolated and separated from the adjacent vagus nerve, and the pterygopalatine artery is ligated close to its origin. The tip of a 4-cm length of 3-0 monofilament nylon suture (Harvard Apparatus) is rounded by burning to achieve a tip diameter of 0.33-0.36 mm and tip length of 0.5-0.6 mm and coated with poly-L-lysine. The suture is introduced through the CCA and advanced into the ICA and thence into the circle of Willis (about 18-20 mm from the carotid bifurcation), effectively occluding the middle cerebral artery. The silk suture around the CCA is tightened around the intraluminal nylon suture to secure it and permanently occlude the middle cerebral artery.

EXAMPLES

Example 1

Impact of Gender on the Neuroprotective Efficacy of Tat-NR2B9c

The neuroprotective efficacy of Tat-NR2B9c was assessed in both male and female rats using the in vivo pial 3 vessel occlusion (P3VO) model of stroke (Forder J P, Munzenmaier D H, Greene A S. Angiogenic protection from focal ischemia with angiotensin II type 1 receptor blockade in the rat. Am J Physiol Heart Circ Physiol 2005 April; 288(4): H1989-H1996).

Methods

Animals

Adult Sprague Dawley rats (10-12 weeks old) (males ~300 g, females ~250 g) were fasted for 12-18 hours before being subjected to permanent pial vessel occlusion of 3 terminal branches of the Middle Cerebral Artery over the Whisker Barrel Cortex (P3VO). Tat-NR2B9c was tested in male rats plus a saline control group (n=8 in each group). Tat-NR2B9c and a saline control were tested in female rats (n=8 in each group). The researcher was blinded to the treatment group during the time of surgery through to the analysis of infarct size.

General Procedure

Rats were anesthetized with a 0.5 ml/kg intramuscular injection of ketamine (100 mg/kg), acepromazine (2 mg/kg), and xylazine (5 mg/kg), supplemented with one third the initial dose as required. An anal temperature probe was inserted and the animal was placed on a heating pad maintained at 37° C. The right external carotid artery (ECA) was cannulated with PE 10 polyethylene tubing for dye injections. The skull was exposed via a midline incision, scraped free of tissue, and the temporalis muscle disconnected from the skull on the right side. Using a dissecting microscope and a pneumatic dental drill, a 6×4 mm cranial window was made over the right somatosensory cortex (2 mm caudal and 5 mm lateral to bregma) by drilling a rectangle through the skull and lifting off the piece of skull while keeping the dura intact. After being bathed with artificial cerebrospinal fluid, small boluses (10 to 20 µL) of the vital dye patent blue violet (10 mmol/L; Sigma) in normal saline, were injected into the right external carotid artery to demonstrate transit through surface vessels of the cortex. Three critical arteriolar branches of the MCA around the barrel cortex were selected and electrically cauterized through the dura. After the cauterizations, the bolus injections and dye transits were repeated to ensure transits through the cauterized arterioles were blocked. The rectangle of skull was replaced over the window and the scalp was sutured. The catheter was removed from the ECA, the ECA was ligated, and the anterior neck was sutured. One hour after initiation of focal occlusion, 0.3 ml of drug (3 nMol/g body weight) or saline control were infused through the tail vein at a rate of 0.06 ml/min. Each rat was returned to its individual cage under a heating lamp to maintain body temperature until the rat fully recovered. Food and water was supplied ad libitum.

Harvesting of Brain Tissue and Infarct Size Analysis

Twenty-four hours post-surgery, animals were re-anesthetized with 1 mL pentobarbital and the brain was quickly harvested. One coronal slice was taken through the infarct region and incubated in 2% triphenyltetrazolium chloride (TTC) for 15 minutes at 37° C. Images were scanned and brain slices were stored at −80° C. Infarct size was measured as a percent of the hemisphere for each rat in the study. After obtaining infarct size measurements, the animals were separated into their respective groups. Comparisons were made between treatment groups as means±SE.

Results and Conclusions

The P3V0 model of stroke in the rat results in a robust and reproducible infarct in both male and female SD rats. The Tat-NR2B9c peptide is neuroprotective in both male and female rats as seen in a significantly decreased infarct size 24 hours after undergoing P3VO surgery (FIG. 1). Treatment with Tat-NR2B9c (3 nM/g) 1 h after stroke dramatically reduced infarcts in animals of both genders (FIG. 1). This neuroprotective response appeared to be more pronounced in females than in males as seen by a complete lack of infarct in female rats treated with the equivalent concentration of Tat-NR2B9c. However saline treated controls indicate that the average infarct size in female rats is smaller (71%) than male rats.

Example 2

Peptides Containing Tat Sequence Induce Mast Cell Degranulation with Histamine Release In Vitro Methods
Cell Culture C57 mice were sterilized with 70% ethanol, and the femur was dissected away from the skin and connective tissue. Bone marrow cells were collected and resuspended in OPTI-MEM (Gibco) containing 5% heat-inactivated FBS, 6% WEHI-conditioned medium (as a source of IL-3), and 55 µM □-2mercaptoethanol. Cells were cultured at approximately $1\times10^6$ cells/mL. After 2 days, cells were collected and centrifuged where the pellet was plated on a fresh plate with fresh medium. New WEHI-condition medium was added each week. The cells were cultured for about 4 weeks after which they were >95% mast cells and were used for the mast cell degranulation assay.

Mast Cell Degranulation Assay

Tryptase activity was determined using the Mast Cell Degranulation Assay Kit (CHEMICON, Temecula, Calif.). After isolation, the cells were washed and resuspended at approximately $1\times10^6$ cells/mL in 1× Assay Buffer. For treatment with Tat-NR2B9c or other peptides, 50 µL of solution of the following concentrations: 0.125 mg/mL, 1.25 mg/mL, 12.5 mg/mL, or 125 mg/mL were added to the cell suspension and 500 nM A23187 (Calcimycin), a known inducer of tryptase release in mast cells, was used as a positive control. Cells were incubated at 37° C. and 5% $CO_2$ for 60 minutes. Cell suspension was centrifuged at 700×g and the supernatant was carefully collected. An assay mixture (provided in the kit) was prepared in a 96-well microtiter plate. The colorimetric reaction was initiated by adding 20 µL of the Tryptase Substrate to each experimental and control well. Samples were incubated for 60 minutes at 37° C. Optical density was read at 405 nm in a microplate reader.

The following treatments were used to induce mast cell degranulation.
1) Negative control (assay buffer devoid of any peptides)
2) Positive Control (the calcium ionophore A23187
3) Tat-NR2B9c
4) The Tat-derived sequence of Tat-NR2B9c devoid of the PSD-95 binding sequence
5) NR2B9c comprising the PSD-95 binding sequence of Tat-NR2B9c but devoid of the Tat sequence, and
6) AA (a 20 amino-acid peptide comprised of the Tat sequence fused to the 9 carboxy-terminal amino acids of the NMDA NR2B subunit, but with 2 amino acid mutations that make it incapable of binding PSD-95).

All peptides were applied at a concentration of 125 mg/mL in order to approximate the maximal serum concentrations attained in dogs receiving a 10 mg/kg dose of Tat-NR2B9c in some of the animal experiments described below (based on assuming a blood volume of 8% of total body weight).

Results and Conclusions

Figure 2:
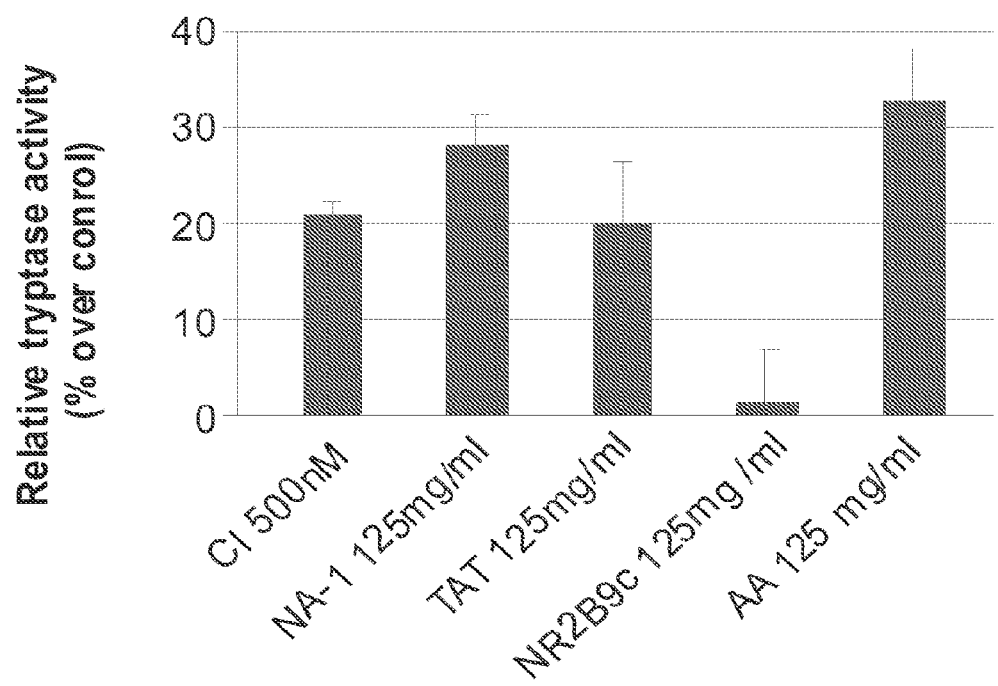
FIG. 2: Peptides containing Tat sequence cause mast cell degranulation. CI: Calcium Ionophore (positive control). NA-1: Tat-NR2B9c, i.e., the peptide YGRKKRRQRRRKLSSIESDV (SEQ ID NO:6), containing both Tat sequence and the 9 carboxy-terminal amino acids of the NR2B subunit. NR2B9c: peptide KLSSIESDV (SEQ ID NO:5), PSD-95 binding sequence of the NMDA NR2B subunit, devoid of the Tat sequence. AA: peptide YGRKKRRQRRRKLSSIEADA (SEQ ID NO:7), identical to Tat-NR2B9c, but with 2 point mutations in the PSD-95 binding domain making it incapable of binding PSD-95. Degranulation was measured by relative tryptase activity (% over control). Bars indicate the means±S.D. of 3-6 independent replicates.

As seen from FIG. 2, peptides containing the Tat transduction domain all caused mast cell degranulation, whereas the NR2B9c peptide, devoid of the Tat sequence, did not. In-vitro mast cell degranulation assays were carried out in the absence of antibodies and therefore, any mast cell degranulation cannot be due to an immune phenomenon. Notably, using RT-PCR and Western blotting, we investigated whether mast cells contained PSD-95 protein, the therapeutic target of Tat-NR2B9c. We were unable to detect PSD-95 in these cells (results not shown), providing further evidence that mast cell degranulation was unlikely to be caused by an interaction of Tat-NR2B9c with PSD-95.

Figure 3:
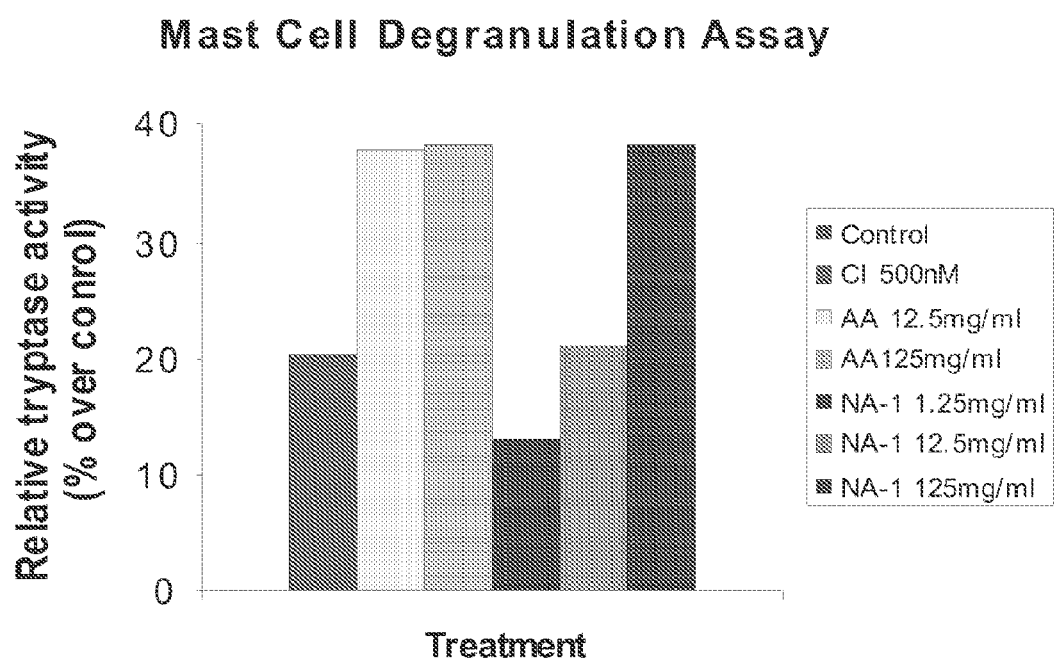
FIG. 3: Mast cell degranulation by peptides containing Tat sequence is dose-dependent. CI: Calcium Ionophore (positive control). NA-1: Tat-NR2B9c, i.e., the peptide YGRKKRRQRRRKLSSIESDV (SEQ ID NO:6), containing both Tat sequence and the 9 carboxy-terminal amino acids of the NR2B subunit. AA: peptide YGRKKRRQRRRKLSSIEADA (SEQ ID NO:7), identical to Tat-NR2B9c, but with 2 point mutations in the PSD-95 binding domain making it incapable of binding PSD-95.

In a further experiment, we determined that the degree of mast cell degranulation by Tat-NR2B9c and by the AA peptide was dose dependent. Specifically, increasing concentrations of Tat-NR2B9c evoked increased mast cell degranulation as shown in FIG. 3.

In further experiments, we investigated the effect of sequence variation in Tat-NR2B9c on mast cell degranulation. Using the same assay, the following compounds were tested (all at 50 µM):

TABLE 5

| Peptide ID | Peptide Name (concentration) | Sequence/Structure |
|---|---|---|
| | control | (No peptide) |
| | CI (500 nM) | Calcium Ionophore |
| | Tat-NR2B9c (125 mg/ml) | YGRKKRRQRRRKLSSIESDV (SEQ ID NO: 6) |
| 1990 | TAT (125 mg/ml) | YGRKKRRQRRR (SEQ ID NO: 2) |
| 1991 | 2B9c (125 mg/ml) | KLSSIESDV (SEQ ID NO: 5) |
| 1992 | AA (125 mg/ml) | YGRKKRRQRRRKLSSIEADA (SEQ ID NO: 7) |
| 1993 | F-Tat-NR2B9c (125 mg/ml) | FGRKKRRQRRRKLSSIESDV (SEQ ID NO: 8) |
| 1994 | Tat-NR2B9c K > A (125 mg/ml) | YGRKKRRQRRRALSSIESDV (SEQ ID NO: 9) |
| 1995 | F-Tat-NR2B9c K > A (125 mg/ml) | FGRKKRRQRRRALSSIESDV (SEQ ID NO: 10) |
| 1992 | AA (12.5 mg/ml) | YGRKKRRQRRRKLSSIEADA (SEQ ID NO: 7) |

Figure 4:
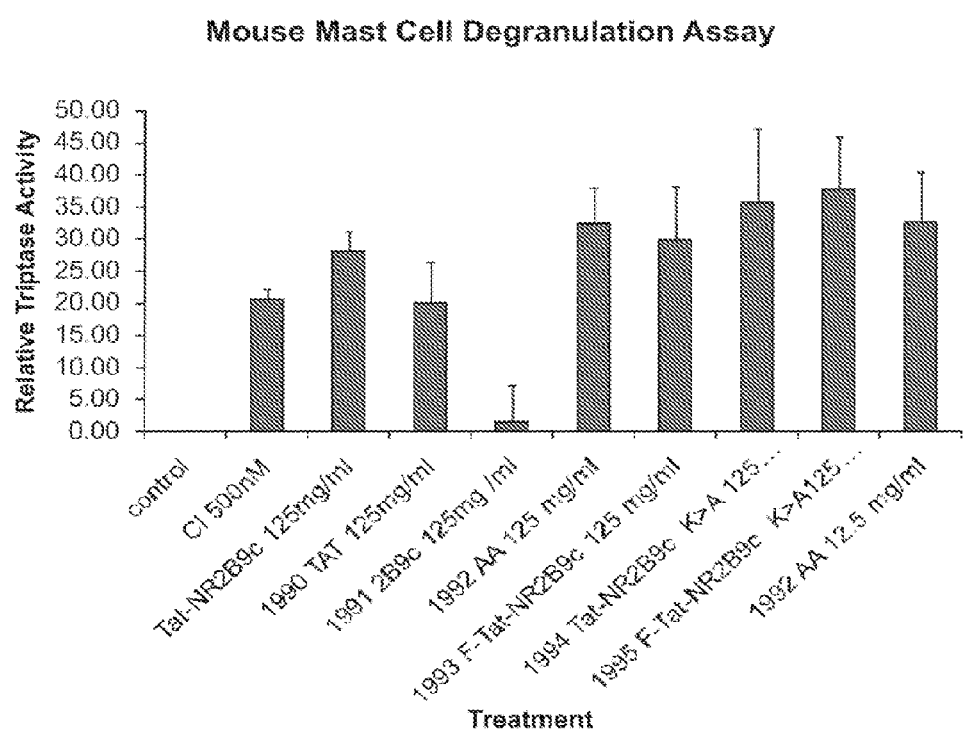
FIG. 4: Mast cell degranulation by peptides containing Tat sequence variants. CI: Calcium Ionophore (positive control). Tat-NR2B9c: the peptide YGRKKRRQRRRKLSSIESDV (SEQ ID NO:6), containing both Tat sequence and the 9 carboxy-terminal amino acids of the NR2B subunit. TAT: Tat peptide sequence YGRKKRRQRRR (SEQ ID NO:2). 2B9c: peptide KLSSIESDV (SEQ ID NO:5), PSD-95 binding sequence of the NMDA NR2B subunit devoid of the Tat sequence. AA: peptide YGRKKRRQRRRKLSSIEADA (SEQ ID NO:7), identical to Tat-NR2B9c, but with 2 point mutations in the PSD-95 binding domain making it incapable of binding PSD-95. F-Tat-NR2B9c: peptide FGRKKRRQRRRKLSSIESDV (SEQ ID NO:8). Tat-NR2B9c K>A: YGRKKRRQRRRALSSIESDV (SEQ ID NO:9). F-Tat-NR2B9c K>A: FGRKKRRQRRRALSSIESDV (SEQ ID NO:10).

As can be seen in FIG. 4, all compounds containing Tat sequence and Tat peptide sequence elicited mast cell degranulation, whereas NR2B9c alone did not elicit this reaction.

Example 3

Figure 5:
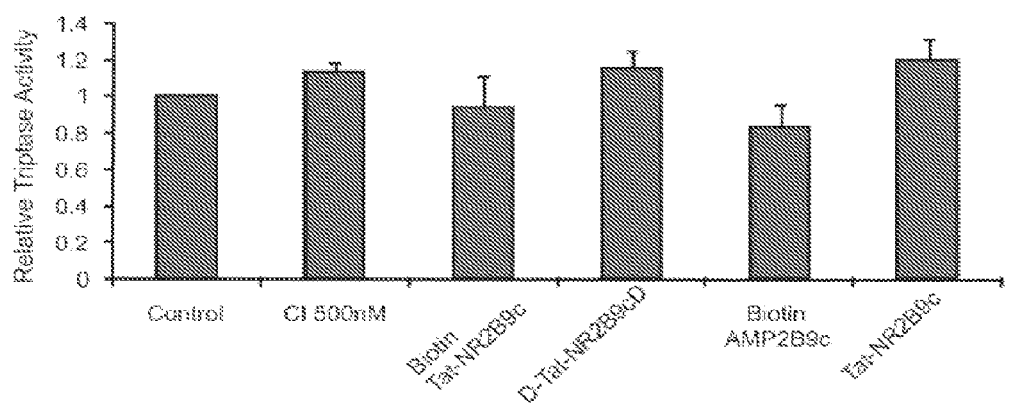
FIG. 5: Conjugates of peptides comprising Tat sequence fail to elicit mast cell degranulation.

Conjugates of Peptides Containing Tat Sequence Fail to Induce Mast Cell Degranulation In Vitro The effect of certain modifications such as conjugation to Tat-containing peptides on mast cell degranulation was studied using methods described in Example 2. The modified peptides included Tat-NR12B9c, the D-isomer of Tat-NR2B9c (termed D-Tat-NR2B9c), a biotin conjugated Tat-NR2B9c, a biotin-conjugated AMP-KLSSIESDV (SEQ ID NO:5). As shown in FIG. 5, biotin-conjugated Tat or AMP peptides to failed to induce mast cell degranulation.

Example 4

Tat-NR2B9c Elicits Increased Histamine Levels and a Histamine Response in Animals Studies in Beagle Dogs A GLP 14-day intravenous toxicity study was conducted in naïve Beagle dogs (3/sex/group) (CRM Study No. 501448) in which animals received daily injections of 0, 0.25, 1.0, or 10 mg/kg of Tat-NR2B9c. Blood samples (approximately 1 mL) were collected from all animals on Days 1, 6 and 12 at predose, 5 and 15 minutes post injection. Blood samples were collected by venipuncture (jugular, saphenous and cephalic) into tubes containing EDTA. The samples were then centrifuged (within 30 minutes of collection) in a refrigerated centrifuge (ca. 4° C.) at 2700 rpm for 10 minutes. Plasma were separated into a second tube with the appropriate label and stored at −80° C. until analysis at CRM. Plasma samples were used for investigating histamine levels. Samples from animals dosed intravenously with Tat-NR2B9c were analyzed using a validated method.

All animals administered 10 mg/kg Tat-NR2B9c displayed treatment-related clinical signs, consisting of a reddening of the muzzle, gums (also noted to be pale), pinna, periorbital region and limbs, and were often associated with swelling. These effects were associated with lethargy and an unpalpable pulse, characterized as a severe hypotensive reaction by the attending veterinarian. These effects were observed daily, starting with the first day of dosing and persisting throughout the 14-day dosing period, with no apparent adaptation by the animals. These effects were not due to the development of an antibody-based immune response, since these animals were not exposed to Tat-NR2B9c by the first day of dosing, and an increased severity of the response over the 14 days of treatment was not observed. Specifically, increased histamine levels were observed immediately following the first administration of Tat-NR2B9c to these naive Beagle dogs (see Table 6 for a summary of the dog plasma histamine levels). These animals had never been exposed to Tat-NR2B9c and thus should not have memory T cells or circulating antibodies against Tat-NR2B9c. Also, no consistent increase in histamine levels was observed during the 14-day repeated dose toxicity study at any dose level, indicating that there is not an expansion of an antigen specific response. Thus, the observed increases in histamine levels due to Tat-NR2B9c are the result of direct degranulation of mast cells rather than an antigen-specific antibody response.

TABLE 6

Determination of Histamine in Dog Plasma by Enzyme Immunoassay DAY 12 Females

| Assay ID | Date | Animal ID | Time Point | Hemo-lyzed sample | Dilution Factor | Final Result (ng/mL) |
|---|---|---|---|---|---|---|
| HIS-16 | 12 Feb. 2006 | 151 | Pre | | 1 | <LLOQ |
| HIS-18 | 3 Mar. 2006 | | 5 min | | 1 | 0.204 |
| | | | 15 min | | 1 | 0.201 |

TABLE 6-continued

Determination of Histamine in Dog Plasma by Enzyme Immunoassay
DAY 12 Females

| Assay ID | Date | Animal ID | Time Point | Hemolyzed sample | Dilution Factor | Final Result (ng/mL) |
|---|---|---|---|---|---|---|
| HIS-10 | 2 Feb. 2006 | 152 | Pre | | 1 | <LLOQ |
| | | | 5 min | | 1 | 0.234 |
| | | | 15 min | | 1 | 0.398 |
| HIS-10 | 2 Feb. 2006 | 153 | Pre | | 1 | 0.187 |
| | | | 5 min | H | 1 | 0.546 |
| | | | 15 min | | 1 | 0.513 |
| HIS-10 | 2 Feb. 2006 | 154 | Pre | | 1 | 0.184 |
| | | | 5 min | | 1 | 0.392 |
| | | | 15 min | | 1 | 0.207 |
| HIS-10 | 2 Feb. 2006 | 155 | Pre | | 1 | <LLOQ |
| | | | 5 min | | 1 | 0.609 |
| | | | 15 min | | 1 | 3.339 |
| HIS-10 | 2 Feb. 2006 | 156 | Pre | | 1 | <LLOQ |
| | | | 5 min | | 1 | 0.190 |
| | | | 15 min | | 1 | <LLOQ |
| HIS-10 | 2 Feb. 2006 | 251 | Pre | | 1 | <LLOQ |
| HIS-16 | 12 Feb. 2006 | | 5 min | | 1 | <LLOQ |
| | | | 15 min | | 1 | 0.273 |
| HIS-10 | 2 Feb. 2006 | 252 | Pre | | 1 | <LLOQ |
| HIS-11 | 3 Feb. 2006 | | 5 min | | 1 | 0.252 |
| | | | 15 min | | 1 | 0.193 |
| HIS-11 | 3 Feb. 2006 | 253 | Pre | | 1 | <LLOQ |
| | | | 5 min | | 1 | 0.213 |
| | | | 15 min | | 1 | 0.293 |
| | | | 5 min | H | 1 | 0.912 |
| | | | 15 min | | 1 | 0.196 |
| HIS-11 | 3 Feb. 2006 | 353 | Pre | | 1 | 0.385 |
| | | | 5 min | H | 1 | 0.282 |
| | | | 15 min | | 1 | 0.446 |
| HIS-12 | 6 Feb. 2006 | 451 | Pre | | 1 | <LLOQ |
| | | | 5 min | H | 3 | 1.642 |
| HIS-17 | 3 Mar. 2006 | | 15 min | | 1 | <LLOQ |
| HIS-12 | 6 Feb. 2006 | 452 | Pre | | 1 | 0.188 |
| | | | 5 min | H | 3 | 6.154 |
| | | | 15 min | H | 3 | 0.565 |
| HIS-12 | 6 Feb. 2006 | 453 | Pre | h | 1 | 0.302 |
| | | | 5 min | | 3 | 13.937 |
| HIS-17 | 3 Mar. 2006 | | 15 min | h | 1 | 0.587 |
| HIS-12 | 6 Feb. 2006 | 454 | Pre | | 1 | <LLOQ |
| HIS-17 | 3 Mar. 2006 | | 5 min | | 1 | 0.504 |
| | | | 15 min | | 1 | 0.312 |
| HIS-12 | 6 Feb. 2006 | 455 | Pre | h | 1 | <LLOQ |
| | | | 5 min | h | 3 | 2.335 |
| HIS-17 | 3 Mar. 2006 | | 15 min | | 1 | 0.312 |
| HIS-18 | 3 Mar. 2006 | 456 | Pre | | 1 | 0.351 |
| | | | 5 min | h | 1 | 0.485 |
| HIS-16 | 12 Feb. 2006 | | 15 min | | 1 | 0.330 |

LLOQ = 0.180 ng/mL
h = sample was hemolyzed

Cardiovascular Effects of Tat-NR2B9c Indicative of Histamine Release in Dogs

In a GLP cardiovascular telemetry study in unrestrained conscious Beagle dogs (CRM Study No. 691106), 6 animals (3 males, 3 females) were administered escalating doses of Tat-NR2B9c (0.25, 1.0, or 5.0 mg/kg gross peptide), with a washout period of 3 days between dose levels. No effects on blood pressure were observed at 0.25 or 1.0 mg/kg. A transient drop in blood pressure was observed in 4 of 6 dogs at 5 mg/kg, lasting approximately 30 minutes. The finding that a drop in blood pressure may have been dose-related indicates that the drop was not due to an allergic (antibody mediated) immune response. Moreover, the time-frame between the low dose (0.25 mg/kg) and the high dose (5.0 mg/kg) was about 6 days, i.e., of insufficient duration to allow the generation of an immune response. The effect is thus caused by a direct degranulation of mast cells causing histamine release.

To obtain detailed cardiovascular information at the highest dose level tested in the 14-day dog repeated-dose toxicity study (i.e., 10 mg/kg), an additional GLP cardiovascular telemetry study in unrestrained, conscious, Beagle dogs was performed (CRM Study No. 691429). Six animals (3 males, 3 females) received vehicle in the morning and 10 mg/kg Tat-NR2B9c in the afternoon of the same day (at least 4 hours between doses). Increases in heart rate were observed for up to 15 minutes post-dose in treated animals, with the maximum effect observed at 10 minutes in males and females. Decreases in blood pressure values (up to 62%) were observed in individual animals at 5 to 10 minutes post-dose. The female animals used in this additional cardiovascular study were obtained from the Charles River colony and were non-naïve animals that had been previously used in the first cardiovascular study for Tat-NR2B9c (CRM Study No. 691106). The effects observed at 10 mg/kg in CRM Study No. 691429 were comparable to the clinical signs observed in the 14-day dog toxicity study (CRM Study No. CRM Study No. 501448), with more severe blood pressure effects observed for treated animals than that observed at the highest dose level (5 mg/kg) tested in CRM Study No. 691106. These results again indicate a direct degranulation of mast cells.

We conducted non-GLP studies of the effects of Tat-NR2B9c on blood pressure in anesthetized rats receiving 50 mg/kg of Tat-NR2B9c. This dose was selected for the rat as it produced decreased tidal volume, respiratory rate and derived minute volume. In one experiment, 5 male Sprague-Dawley rats received a 50 mg/kg Tat-NR2B9c bolus dose over 3 minutes. Blood pressure was monitored via a femora arterial catheter.

Figure 6:
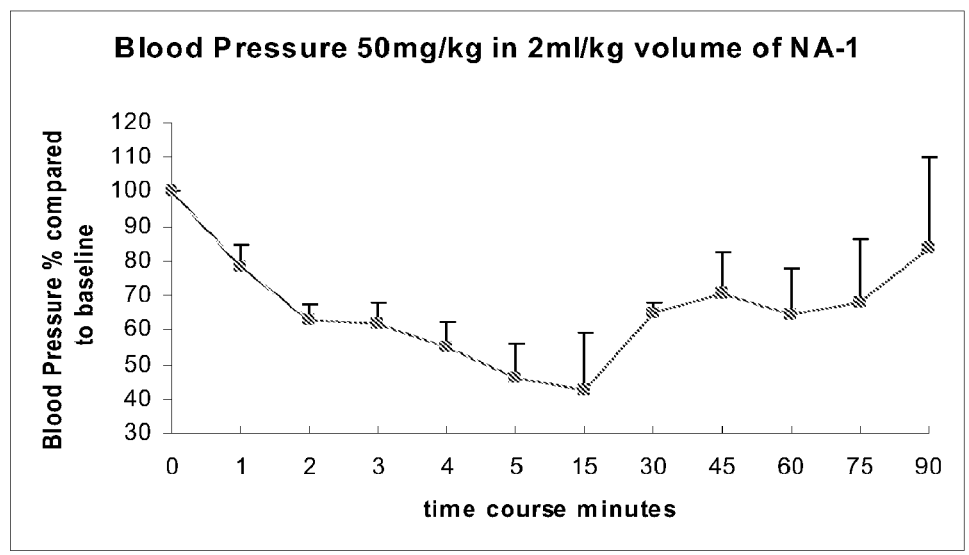
FIG. 6: Observed drop in blood pressure observed after administration of 50 mg/kg Tat-NR2B9c to beagle dogs.

All animals experienced transient reductions in mean arterial pressure as shown in FIG. 6. Another experiment, in which 6 animals were similarly tested, showed similar results. As discussed above in the case of dogs, these reactions in rats were also observed in naïve animals that had not had any prior opportunity to develop an immune response to Tat-NR2B9c. These data provide evidence in a second species of mast cell degranulation by peptides containing Tat sequence.

Inflammatory Reactions Indicative of Histamine Release in Dogs

A non-GLP study was conducted to examine a dose range for Tat-NR2B9c, administered to Beagle dogs by a single, slow intravenous injection. Two animals (one male and one female Beagle dog) were dosed intravenously with Tat-NR2B9c on seven occasions. There was a 3-4 day wash-out period between the doses. The first dose was given at 2.5 mg/kg. Since the animals did not show any signs of toxicity, the second dose was administered at 7.5 mg/kg. The male animal displayed angio-neurotic edema of the soft tissue of the head and urticaria type of reaction, especially on the ventral aspect of the abdomen. There was no reaction in the female dog. Vital signs (heart rate, blood pressure, respiratory rate and body temperature) stayed within the normal physiological ranges in both animals. The third dose was given at 12.5 mg/kg. After dosing, angio-neurotic oedema and urticaria were observed in both animals. The reaction in the male dog was assessed to be moderate, and in the female animal, the reaction was mild. The next dose was set at 20.0 mg/kg. After dosing, the male animal went into shock, where blood pressure (BP) and pulse were undetectable. The animal was treated with i.v. administration of benadryl and dexamethasone. BP at 5 minutes post-dosing was recorded as 37/13 mm Hg (normal BP in a dog is ~160/90). A decision was made not to dose the female animal.

The next doses were given in order to better understand the type of reactions seen in preceding doses. The fifth and sixth doses were set at 2.5 and 5.0 mg/kg. At 2.5 mg/kg with the exception of reddening of ear and face of the male dog, no other adverse reactions were observed in either dog. At 5.0 mg/kg, a moderate reaction was seen in the male animal, while there was no reaction in the female dog.

It was concluded that Tat-NR2B9c at high doses is capable of inducing profound transient hypotension and urticaria-like skin reactions. These reactions appeared to be dose dependent, and the male animal appeared to be more sensitive to the test article than the female animal.

Example 5

Treatment with Antihistamine Prevents Symptoms Induced by Tat-NR2B9c in Dogs

Both animals from Example 4 were next administered 12.5 mg/kg of Tat-NR2B9c after pre-treatment with benadryl at 1 mg/kg administered 30 minutes before Tat-NR2B9c. There was slight reddening of inner skin of the ears in the male animal. The male animal also vomited ~15-20 minutes after the administration of Tat-NR2B9c. There was no reaction observed in the female dog. Accordingly, pretreatment with the antihistamine drug benadryl prevented the angio-neurotic oedema and urticaria reactions that were earlier observed in both animals at the same dose level of Tat-NR2B9c. The results indicate that antihistamines such as benadryl, and of corticosteroids such as dexamethasone effectively treat the adverse consequences of mast cell degranulation.

Taken together, these results provide direct experimental evidence that administration of Tat-NR2B9c elicits an elevation in blood histamine levels in experimental animals, that increased histamine levels are due to mast cell degranulation, and that treating this response with antihistamine medications and with corticosteroids may constitute and effective means by which to administer Tat-NR2B9c and other compounds containing protein translocation domains such as Tat.

Example 6

Direct Evidence that Tat-NR2B9c Elicits Blood Histamine Elevations in Humans

Methods

We carried out a Safety, Tolerability and Pharmacokinetic Study of Tat-NR2B9c in humans. Subjects were either normal, healthy, non-smoking males or post-menopausal or surgically sterile female subjects with a minimum age of 18 years. The subjects were either administered Tat-NR2B9c, Lot #: 124-134-001B, or were given placebo (Phosphate Buffered Saline), Lot #: 124-134-001A, administered as an intravenous infusion (10±1 minutes). Four subjects were dosed in each of Cohorts 1 to 3, and 10 subjects were dosed in each of Cohorts 4 to 8. All 62 subjects completed the study. Treatment periods for each cohort were as follows: Cohort 1: Sep. 14, 2006; Cohort 2: Sep. 26, 2006; Cohort 3: Oct. 6, 2006; Cohort 4: Oct. 20, 2006; Cohort 5: Nov. 6, 2006; Cohort 6: Dec. 4, 2006; Cohort 7: Dec. 17, 2006; Cohort 8: Feb. 25, 2007.

Blood Draw Timepoints:

During the study period, 11 blood samples were collected for pharmacokinetic analysis from each subject at the following timepoints: 0.00 (pre-dose), 0.08 (5 minutes), 0.17 to 0.25 (10 to 15 minutes, precisely at the end of each individual drug infusion), 0.33 (20 minutes), 0.50, 0.75, 1.00, 2.00, 6.00, 12.00, and 24.00 hours post-dose. In addition, 8 blood samples were collected for histamine analysis from each subject at the following timepoints: 0.00 (pre-dose), and at 0.08 (5 minutes), 0.17 (10 minutes), 0.25, 0.50, 1.00, 2.00, and 24.00 hours post-dose.

Safety Assessment:

The safety assessment was performed on all subjects who received at least 1 dose during the course of the study. The incidents of all adverse events (AEs) were tabulated by treatment and subject number. Absolute values for vital signs, electrocardiogram (ECG) parameters, laboratory parameters and physical examinations were also documented and values outside the normal range were flagged. Shifts from baseline values were tabulated. AEs were documented using investigator and Medical Dictionary for Regulatory Activities (MedDRA) terms.

Results

Part 1: Effects of Tat-NR2B9c on Blood Histamine Levels:

A summary of abnormal histamine results by dose is illustrated in Table 7. Seven of 8 subjects in the 3.75 mg/kg dose group had histamine levels greater than 10 nmol/L (average 24.3 nmol/L; maximum of 39.8 nmol/L) 10 minutes after the start of NA 1 administration, and 3 of the subjects still had histamine levels greater than 10 nmol/L (average 15.3 nmol/L; maximum of 20.3 nmol/L) 15 minutes after the start of NA 1 administration.

Other than the 3.75 mg/kg dose group, no treatment group had significant abnormal levels of histamine. The placebo group and the 0.375 mg/kg dose group each had 1 subject that had an elevated histamine level at 1 timepoint, but these results were at screening and at 2.00 hours post dose, respectively. All abnormal histamine results returned to the normal range within 24.00 hours of drug administration.

TABLE 7

Number of Subjects with Histamine levels >10 nmol/L by Treatment Group

| | | Number of Subjects | | | | | | | | |
|---|---|---|---|---|---|---|---|---|---|---|
| | | | | | Dose of NA-1 (mg/kg) | | | | | |
| Day | Time (hr) | Placebo (n = 16) | 0.02 (n = 2) | 0.08 (n = 2) | 0.20 (n = 2) | 0.375 (n = 8) | 0.75 (n = 8) | 1.50 (n = 8) | 2.60 (n = 8) | 3.75 (n = 8) |
| Screening | N/AP | 0 | 0 | 0 | 0 | 1 | 0 | 0 | 0 | 0 |
| 1 | 0.00 | 0 | 0 | 0 | 0 | 0 | 0 | 0 | 0 | 0 |
| | 0.08 | 0 | 0 | 0 | 0 | 0 | 0 | 0 | 0 | 0 |
| | 0.17 | 0 | 0 | 0 | 0 | 0 | 0 | 0 | 0 | 7 |
| | 0.25 | 0 | 0 | 0 | 0 | 0 | 0 | 0 | 0 | 3 |
| | 0.50 | 0 | 0 | 0 | 0 | 0 | 0 | 0 | 0 | 0 |

TABLE 7-continued

Number of Subjects with Histamine levels >10 nmol/L by Treatment Group

Number of Subjects

Dose of NA-1 (mg/kg)

| Day | Time (hr) | Placebo (n = 16) | 0.02 (n = 2) | 0.08 (n = 2) | 0.20 (n = 2) | 0.375 (n = 8) | 0.75 (n = 8) | 1.50 (n = 8) | 2.60 (n = 8) | 3.75 (n = 8) |
|---|---|---|---|---|---|---|---|---|---|---|
|  | 1.00 | 0 | 0 | 0 | 0 | 0 | 0 | 0 | 0 | 0 |
|  | 2.00 | 1 | 0 | 0 | 0 | 0 | 0 | 0 | 0 | 0 |
|  | 24.00 | 0 | 0 | 0 | 0 | 0 | 0 | 0 | 0 | 0 |
| 7 | N/AP | 0 | 0 | 0 | 0 | 0 | 0 | 0 | 0 | 0 |
| 14 | N/AP | 0 | 0 | 0 | 0 | 0 | 0 | 0 | 0 | 0 |
| 28 End-of-study | N/AP | 0 | 0 | 0 | 0 | 0 | 0 | 0 | 0 | 0 |

Part 11: Safety Data

Forty subjects who participated in the study experienced a total of 168 adverse effects (AEs) during the study. The majority of AEs were mild in severity. Thirty-four of 46 active treatment subjects (73.9%) experienced at least 1 AE, while 6 of 16 placebo treatment subjects (37.5%) experienced at least 1 AE. Subjects in the 2.60 and 3.75 mg/kg dose groups experienced significantly more AEs than subjects in the lower dose groups. No Serious Adverse Events (SAEs) were reported. The most common AEs experienced by subjects receiving Tat-NR2B9c were feeling hot (13/46; 28.3%), pruritus (12/46; 26.1%), flushing (10/46; 21.7%), and dry mouth (9/46; 19.6%). All AEs were resolved with the exception of 2 instances of increased blood glucose, as the subjects were lost to follow-up.

The incidence of AEs in the 2.60 and 3.75 mg/kg dose groups was higher than the AE incidence rate in the placebo, 0.02, 0.08, 0.20, 0.375, 0.75 and 1.50 mg/kg dose groups. At doses of Tat-NR2B9c≥2.60 mg/kg, several AEs were frequently reported. These included: (1) decreases in blood pressure, (2) tingling sensation (paraesthesia), (3) numbness (hypoaesthesia), (4) redness (erythema), (5) rash, (6) itchiness (pruritus), (7) dry mouth, (8) nausea, (9) feeling hot, and (10) flushing. The onset of these AEs coincided with the administration of the study drug and was probably related to the study drug.

In preclinical trials with Tat-NR2B9c, elevated histamine levels were observed in high dose groups, and were likely the source of side effects including swelling, redness and hypotension. In the current study, histamine levels were elevated in 7 of the 8 subjects in the highest dose group (3.75 mg/kg) 10 minutes after the start of the intravenous drug administration, and remained elevated in 3 of these subjects 15 minutes after drug administration, after which time levels returned to the normal range. During the same time frame that histamine levels were elevated, most of the AEs in the 3.75 mg/kg dose group were observed. This suggests that the elevated histamine levels were the source of the most frequently reported AEs (including decreased blood pressure, tingling, numbness, redness, rash, itchiness, dry mouth, nausea, feeling hot, and flushing).

Most of the listed AEs were also observed in preclinical animal trials where the Maximum Tolerated Dose (MTD) was established at 12.5 and 100 mg/kg for dogs and rats, respectively. Most of the AEs in the 2.60 and 3.75 mg/kg dose groups were not observed, or observed in only 1 subject in the dose groups between 0.02 and 1.50 mg/kg. This suggests that the AEs that were observed at higher doses of Tat-NR2B9c were minimal or not present at this lower dose range.

Example 7

Materials

TAT-NR2B9c chemically synthesized by AnaSpec Inc (San Jose, Calif.). Rv-Tat-NR2B9c chemically synthesized by Sickkids Hospital Advanced Protein Technology Centre (Toronto, ON, Canada). All peptides were high-performance liquid chromatography purified to >95%. Peptide stocks (3 mM) were prepared in sterile saline and stored in aliquots at −80° C. Cromolyn, pyrilamine, ranitidine, oxatomide and Dexamethasone purchased from Sigma-Aldrich (St. Louis, Mo.)

Rat were put to sleep in a chamber with 2% isoflurane and a gas of 2 L oxygen, and then transferred to a face mask with reduced gas (1% isoflurane and a gas of 2 L oxygen) once asleep. Femoral cut down of artery and vein for catheterization with PE50 tubing. These arteries and veins provide access for continual monitoring of mean arterial pressure (MAP) and for drug infusion respectively. Cromolyn (1 mg/kg/min) or saline (1 ml/kg/min) was infused at for 5 minutes then TAT-NR2B9c, Rv-Tat-2B9c (3 µM/kg in saline) or saline (1 ml/kg) was give by bolus injections immediately after saline or cromolyn infusion. Other drugs using these studies were infused 10 minutes before TAT-NR2B9c injection. Surgeries were done on animal's the left side. Animal's blood pressure (HEWLETT PACKARD Blood pressure system, model 78304A) and body temperature (Digi Sense Thermometer, model 8528-10) was monitored every 1 minute within 60 minutes. Saline (1 ml/kg) was given to all groups at baseline, and the control group received a further 2 ml/kg saline at each time point. Results presented are the average MAP from 5 rats. A summary of all experiments performed (n=10 each drug) is presented in the respective graphs as mean±SEM, (Student's test, *, $P<0.05$ and ***, $p<0.001$)

FIG. 7 shows that both Tat-NR2B9c and Rv-Tat-NR2B9 (tat attached to NR2B9c in reverse orientation) at the high dose of 7.5 mg/kg give a rapid and transient reduction in MAP over a period of about 0-6 min after injection.

FIGS. 8A-D show the effect of 5 mg/kg cromolyn administered intravenously about five minutes before the administration of Tat-NR2B9c. FIG. 8A shows a time course of MAP for treatment with Tat-NR2B9c alone, treatment with Tat-NR2B9c plus cromolyn or treatment with cromolyn.

plus saline as a control. FIG. 8B shows areas under the curve. FIG. 8C shows minimal MAP value. FIG. 8D shows maximum percentage decline in MAP. Asterisks indicated a statistically significant result. FIG. 8B shows that treatment with cromolyn significantly reduces the decline in MAP due to Tat-NR2B9c. Cromolyn did not itself affect MAP in the absence of Tat-NR2B9c as shown by the cromolyn saline control. The comparisons shown in FIGS. 8B-D further illustrate the significant effect of cromolyn in inhibiting decline of blood pressure.

The same experiment was performed with Rv-Tat-NR2B9c used in place of Tat-NR2B9c and similar results were obtained as shown in FIGS. 8E and F. That is, cromolyn significantly inhibited decline of MAP values due to Rv-Tat-NR2B9c.

FIGS. 9A-D present similar data except that diphenhydramine (12.5 mg/kg) (Benadryl), a histamine H1 antagonist, was used as an anti-inflammatory agent in place of cromolyn. Diphenhydramine also significantly inhibited decline in blood pressure as shown in FIGS. 9A, B and D. However, administration of diphenhydramine itself caused a sharp reduction in blood pressure before Tat-NR2B9c was administered. The experiment was repeated except that diphendydramine was used at 1 mg/kg. Diphendydramine was not observed to have a significant effect on inhibiting decline of blood pressure due to Tat-NR2b9c at this dosage. Diphendydramine also did not itself reduce blood pressure at this dosage.

The experiment was repeated with another H1 antagonist pyrilamine. Although the maximal decline in blood pressure due to Tat-NR2B9c was slightly reduced, the reduction did not achieve statistical significance (see FIGS. 10 A-D).

FIG. 11A presents similar data for a combination of diphenhydramine (12.5 mg/kg) and H2 antagonist Ranitidine (10 mg). The combined agents themselves lowered MAP (presumably due to the effect of diphenhydramine and inhibited reduction due to Tat-NR2B9c. The inhibition of reduction was significant as shown by the analyses in FIGS. 11B-D. The experiment was repeated using only Ranitidine. Ranitidine had no effect on MAP itself and any effect in inhibiting decline of MAP due to Tat-NR2B9c was slight and not statistically significant.

A similar experiment was performed with 6 mg/kg dexamethasone as the anti-inflammatory agent. Dexamethasone was administered about ten min before TAT-NR9B9c. Dexamethasone was not observed to have a significant effect on inhibiting decline in blood pressure due to Tat-NR2B9c in this experiment.

A similar experiment was performed with 6 mg/kg lodoxamide co-formulated with 3 mg/kg Tat-NR2B9c compared with 3 mg/kg Tat-NR2B9c. Solution made fresh by combining 1.89 ml 20 mg/ml Tat-NR2B9c in 0.9% saline with 3.11 ml 0.1% Alomide® (lodoxamide) and vortexing. Each mL of ALOMIDE® contains: 1.78 mg lodoxamide tromethamine equivalent to 1 mg lodoxamide, preservative benzalkonium chloride 0.007%, mannitol, hydroxypropyl methylcellulose 2910, sodium citrate, citric acid, edetate disodium, tyloxapol, hydrochloric acid and/or sodium hydroxide (to adjust pH), and purified water.

Figure 13A:
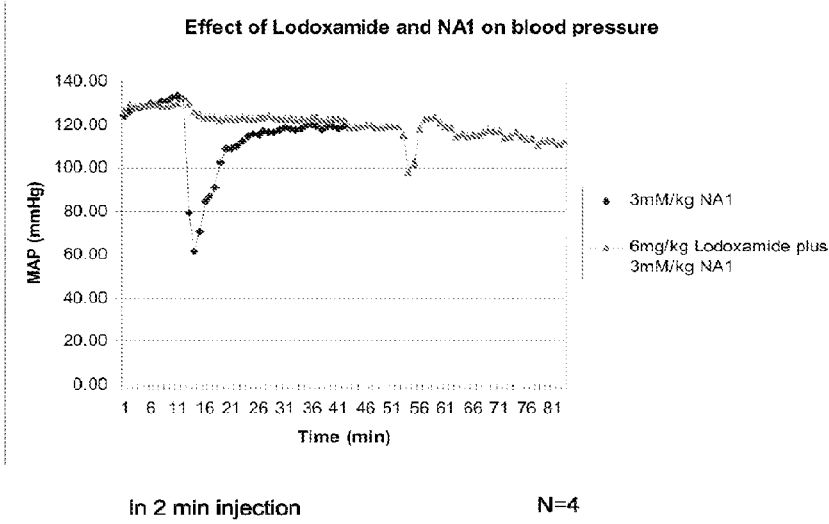
FIGS. 13A and 13B show a lodoxamide co-formulation with Tat-NR2B9c and cromolyn administered immediately before Tat-NR2B9c completely abrogate a drop in MAP due to Tat-NR2B9c.
Figure 13B:
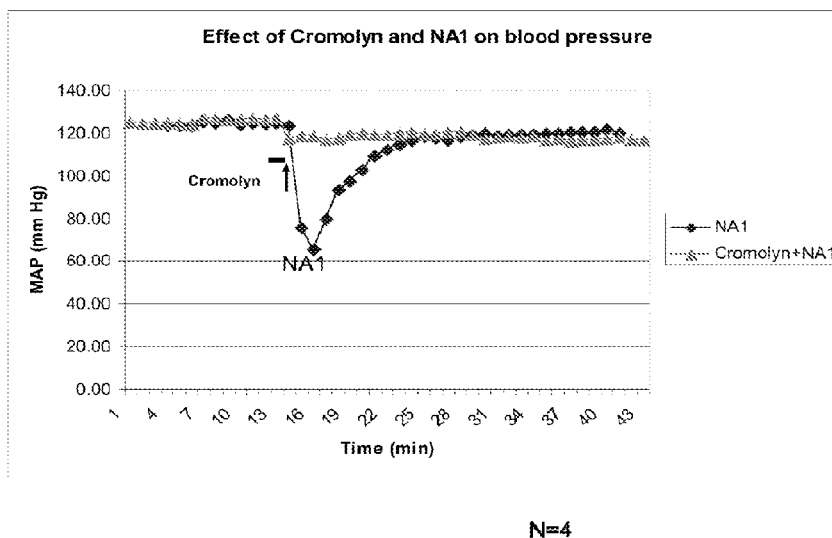

The co-formulation was stable. By contrast, a co-formulation of Tat-NR2B9c with cromolyn tended to precipitate. Animals (male, Sprague Dawley) were allowed to eat and drink before surgery. Animals were put to sleep in a chamber with 2% isoflurane and 1 L oxygen. Once asleep, rat was transferred to a face mask at 1% isoflurane and a gas of 1 L oxygen. PESO tubing was used for connection of the femoral artery and vein. These arteries and veins provide access for continual monitoring of arterial pressure and for drug infusion (50 mg per kg in a volume of 2 ml per kg injected with in 2 minutes). Surgeries were done on the left side. Animal's blood pressure and body temperature was monitored for 90 minutes. FIG. 13A shows a MAP timecourse following either a 2 minute infusion of 3 mM/kg Tat-NR2B9c with 6 mg/kg Lodoxamide (Mast cell stabilizer) or 3 mM/kg Tat-NR2B9c alone as a control in a 2 ml volume. Co-treatment with lodoxamide can completely abrogate the drop in MAP resulting from Tat-NR2B9c injection. Cromolyn infused for three minutes immediately before administration of TAT2B9c also completely abrogated the drop in MAP (FIG. 13B).

Example 8

Rv-Tat-NR2B9c was compared with Tat-NR2B9c in a model of ischemia. Rv-Tat-NR2B9c is the same as Tat-NR2B9c except that the order of amino acids from N—C in the tat portion of the peptide is reversed in Rv-Tat-NR2B9c.

Methods for Three pial vessel occlusion model of ischemia (3PVO): Experiments were performed on fasted rats (free overnight access to water but not food). Permanent three pial vessels occlusion (3PVO) was performed as described by Forder et al., Am. J. Physiol. Heart Circ. Physiol. 2005 April; 288(4):H1989-96. In brief, rats were anesthetized with a 0.5 ml/kg intramuscular injection of ketamine (100 mg/kg), acepromazine (2 mg/kg), and xylazine (5 mg/kg), supplemented with one-third of the initial dose as required. A rectal temperature was monitored and the animal body temperature was maintained at 37° C. by using a heating pad. The skull was exposed via a midline incision and scraped free of tissue. Using a dissecting microscope and a pneumatic dental drill, a 6- to 8-mm rectangular cranial window was made over the right somatosensory cortex (2 mm caudal and 5 mm lateral to bregma) and the loose piece of skull was removed while keeping the dura intact. The 3 pial arteriolar middle cerebral artery branches were electrically cauterized around the barrel cortex area. Incision was sutured with 3.0 silk sutures. Animals were returned to individual cages under a heating lamp to maintain body temperature until the rats fully recovered. Food and water was supplied. One hour after 3PVO ischemia the rats were injected with 3 μM/kg Tat-NR2B9c or Rv-Tat-NR2B9c intravenously through tail vein. Twenty-four hours after surgery, the brain was quickly harvested, sliced (2 mm thick) and incubated in 2% triphenyltetrazolium chloride (TTC) (Sigma-Aldrich, St. Louis, Mo.) in saline for 15 min at 37° C. Images were scanned (CanoScan, 4200F, Canon). Infarct percentage was calculated per slice using Image J software (NIH).

Figure 14:
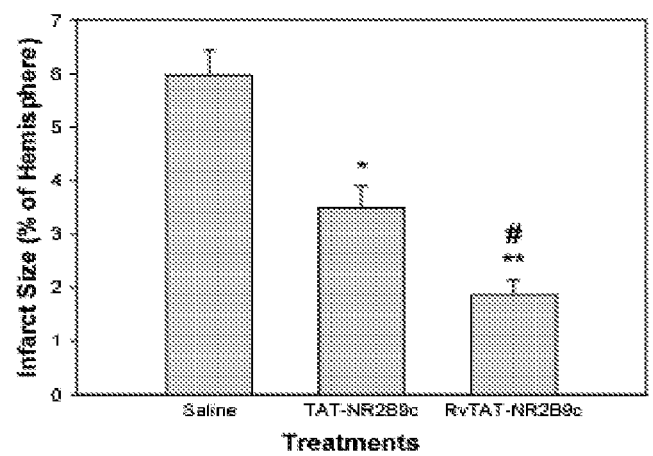
FIG. 14 show that Rv-NR2B9c is effective in reducing infarcts in an animal model of cerebral ischemia.

Rv-Tat-NR2B9c is as or more effective than Tat-NR2B9c at reducing infarcts in the 3PVO model. FIG. 14 shows a bar graph showing the average infarct size for each group.

Example 9

Figure 15:
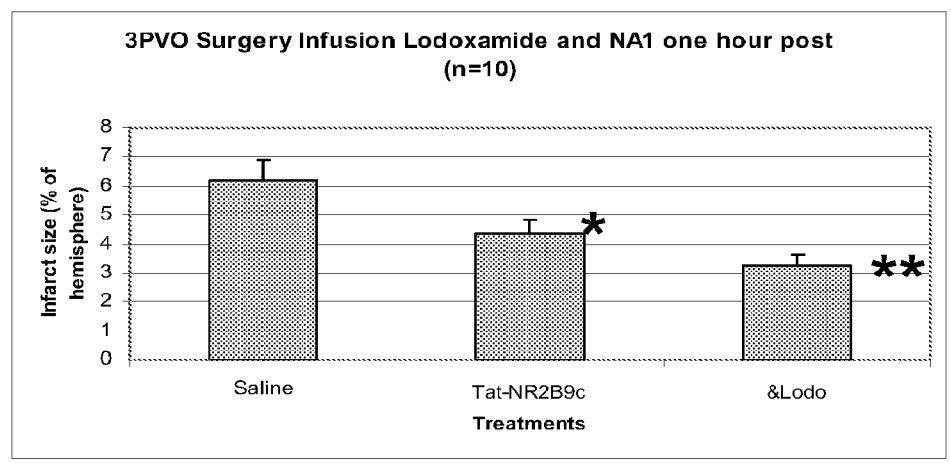
FIG. 15 shows that Tat-NR2B9c in combination with lodoxamide resulted in a statistically significant reduction relative to Tat-NR2B9c alone.

A co-formulation of lodoxamide and Tat-NR2B9c as described above was tested in comparison with Tat-NR2B9c and vehicle controls was tested on a rat 3PVO model of stroke as described above. The area of resulting infarctions is shown in FIG. 15. Tat-NR2B9c significantly inhibited infarction size relative to vehicle control. However, surprisingly the lodoxamide Tat-NR2B9c combination resulted in a statistically significant reduction relative to Tat-NR2B9c alone. Thus, peripheral co-administration of lodoxamide not only reduces inflammation due to Tat-NR2B9c but also increases its efficacy in reducing infarcts.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. To the extent difference sequences might be associated with the same accession number at different times, the sequence associated with the accession number at the effective filing date is meant. The effective filing date means the earliest priority date at which the accession number at issue is disclosed. Unless otherwise apparent from the context any element, embodiment, step, feature or aspect of the invention can be performed in combination with any other.

What is claimed is:

1. A co-formulation comprising lodoxamide and a peptide having an amino acid sequence of SEQ ID NO:6 (YGRK-KRRQRRRKLSSIESDV) and water.

2. The co-formulation of claim 1 in which less than 5% by weight of the lodoxamide and less than 5% by weight of the peptide is in particulate form.

3. The co-formulation composition of claim 1 further comprising sodium chloride at a concentration of 50-200 mM.

4. The co-formulation of claim 1, wherein the concentration of lodoxamide is 0.5-1 mg/ml and the concentration of the peptide is 5-20 mg/ml.

* * * * *

SEQUENCE LISTING

```
<160> NUMBER OF SEQ ID NOS: 72

<210> SEQ ID NO 1
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 3

Phe Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic tat peptide

<400> SEQUENCE: 4

Gly Arg Lys Lys Arg Arg Gln Arg Arg Arg Pro Gln
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic pharmacologic agent

<400> SEQUENCE: 5

Lys Leu Ser Ser Ile Glu Ser Asp Val
1               5
```

-continued

```
<210> SEQ ID NO 6
<211> LENGTH: 20
<212> TYPE: PRT
<213> ORGANISM: Artificial Sequence
<220> FEATURE:
<223> OTHER INFORMATION: Synthetic Tat-NR2B9c peptide

<400> SEQUENCE: 6

Tyr Gly Arg Lys Lys Arg Arg Gln Arg Arg Lys Leu Ser Ser Ile
1               5                   10                  15

Glu Ser Asp Val
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Tat-NR2B9c peptide with 2 point
      mutations in the PSD-95 binding domain

<400> SEQUENCE: 7

Tyr Gly Arg Lys Lys Arg Arg Gln Arg Arg Lys Leu Ser Ser Ile
1               5                   10                  15

Glu Ala Asp Ala
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic F-Tat-NR2B9c peptide

<400> SEQUENCE: 8

Phe Gly Arg Lys Lys Arg Arg Gln Arg Arg Lys Leu Ser Ser Ile
1               5                   10                  15

Glu Ser Asp Val
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Tat-NR2B9c K>A peptide

<400> SEQUENCE: 9

Tyr Gly Arg Lys Lys Arg Arg Gln Arg Arg Ala Leu Ser Ser Ile
1               5                   10                  15

Glu Ser Asp Val
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic F-Tat-NR2B9c K>A peptide

<400> SEQUENCE: 10

Phe Gly Arg Lys Lys Arg Arg Gln Arg Arg Ala Leu Ser Ser Ile
1               5                   10                  15

Glu Ser Asp Val
```

```
<210> SEQ ID NO 11
<211> LENGTH: 20
<212> TYPE: PRT
<213> ORGANISM: Artificial Sequence
<220> FEATURE:
<223> OTHER INFORMATION: Synthetic C-terminal 20-mer sequence of
      NMDAR2B

<400> SEQUENCE: 11

Phe Asn Gly Ser Ser Asn Gly His Val Tyr Glu Lys Leu Ser Ser Ile
1               5                   10                  15

Glu Ser Asp Val
            20

<210> SEQ ID NO 12
<211> LENGTH: 4
<212> TYPE: PRT
<213> ORGANISM: Artificial Sequence
<220> FEATURE:
<223> OTHER INFORMATION: Synthetic PL motif of NMDAR2B

<400> SEQUENCE: 12

Glu Ser Asp Val
1

<210> SEQ ID NO 13
<211> LENGTH: 20
<212> TYPE: PRT
<213> ORGANISM: Artificial Sequence
<220> FEATURE:
<223> OTHER INFORMATION: Synthetic C-terminal 20-mer sequence of NMDAR1,
      NMDAR1-1, NMDAR1-4, NMDAR1-3b, NMDAR1-4b

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic C-terminal 20-mer sequence of
      NMDAR1-2, NMDAR1-3

<400> SEQUENCE: 14

Arg Arg Ala Ile Glu Arg Glu Glu Gly Gln Leu Gln Leu Cys Ser Arg
1               5                   10                  15

His Arg Glu Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic C-terminal 20-mer sequence of NMDAR2C

<400> SEQUENCE: 15

Thr Gln Gly Phe Pro Gly Pro Cys Thr Trp Arg Arg Ile Ser Ser Leu
1               5                   10                  15
```

Glu Ser Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic C-terminal 20-mer sequence of NMDAR3A

<400> SEQUENCE: 16

Ala Val Ser Arg Lys Thr Glu Leu Glu Glu Tyr Gln Arg Thr Ser Arg
1               5                   10                  15

Thr Cys Glu Ser
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic C-terminal 20-mer sequence of NMDAR2A

<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic C-terminal 20-mer sequence of NMDAR2D

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor delta 2

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 1

<400> SEQUENCE: 20

```
Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 2

<400> SEQUENCE: 21

Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 3

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 4

<400> SEQUENCE: 23

His Thr Gly Thr Ala Ile Arg Gln Ser Ser Gly Leu Ala Val Ile Ala
1               5                   10                  15

Ser Asp Leu Pro
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 5

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Artificial Sequence
```

```
<220> FEATURE:
<223> OTHER INFORMATION: Synthetic C-terminal 20-mer sequence of
      glutamate receptor 6

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic C-terminal 20-mer sequence of
      glutamate receptor 7

<400> SEQUENCE: 26

Arg Arg Leu Pro Gly Lys Asp Ser Met Ala Cys Ser Thr Ser Leu Ala
1               5                   10                  15

Pro Val Phe Pro
            20

<210> SEQ ID NO 27
<211> LENGTH: 4
<212> TYPE: PRT
<213> ORGANISM: Artificial Sequence
<220> FEATURE:
<223> OTHER INFORMATION: Synthetic C-terminal 4-mer sequence of NMDAR1,
      NMDAR1-1, NMDAR1-4, NMDAR1-3b, NMDAR1-4b

<400> SEQUENCE: 27

Ser Thr Val Val
1

<210> SEQ ID NO 28
<211> LENGTH: 4
<212> TYPE: PRT
<213> ORGANISM: Artificial Sequence
<220> FEATURE:
<223> OTHER INFORMATION: Synthetic C-terminal 4-mer sequence of
      NMDAR1-2, NMDAR1-3

<400> SEQUENCE: 28

His Arg Glu Ser
1

<210> SEQ ID NO 29
<211> LENGTH: 4
<212> TYPE: PRT
<213> ORGANISM: Artificial Sequence
<220> FEATURE:
<223> OTHER INFORMATION: Synthetic C-terminal 4-mer sequence of NMDAR2C,
      NMDAR2D

<400> SEQUENCE: 29

Glu Ser Glu Val
1

<210> SEQ ID NO 30
<211> LENGTH: 4
<212> TYPE: PRT
<213> ORGANISM: Artificial Sequence
<220> FEATURE:
<223> OTHER INFORMATION: Synthetic C-terminal 4-mer sequence of NMDAR3A
```

```
<400> SEQUENCE: 30

Thr Cys Glu Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor delta 2

<400> SEQUENCE: 31

Gly Thr Ser Ile
1

<210> SEQ ID NO 32
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor 1

<400> SEQUENCE: 32

Ala Thr Gly Leu
1

<210> SEQ ID NO 33
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor 2 and glutamate receptor 3

<400> SEQUENCE: 33

Ser Val Lys Ile
1

<210> SEQ ID NO 34
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor 4

<400> SEQUENCE: 34

Ser Asp Leu Pro
1

<210> SEQ ID NO 35
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor 5

<400> SEQUENCE: 35

Glu Thr Val Ala
1

<210> SEQ ID NO 36
<211> LENGTH: 4
<212> TYPE: PRT
```

```
<213> ORGANISM: Artificial Sequence
<220> FEATURE:
<223> OTHER INFORMATION: Synthetic C-terminal 4-mer sequence of
      glutamate receptor 6

<400> SEQUENCE: 36

Glu Thr Met Ala
1

<210> SEQ ID NO 37
<211> LENGTH: 4
<212> TYPE: PRT
<213> ORGANISM: Artificial Sequence
<220> FEATURE:
<223> OTHER INFORMATION: Synthetic C-terminal 4-mer sequence of
      glutamate receptor 7

<400> SEQUENCE: 37

Pro Val Phe Pro
1

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = Glu, Asp, Asn or Gln
<220> FEATURE:
<221> NAME/KEY: MOD_RES
<222> LOCATION: (2)..(2)
<223> OTHER INFORMATION: Xaa = Ser or Thr
<220> FEATURE:
<221> NAME/KEY: MOD_RES
<222> LOCATION: (3)..(3)
<223> OTHER INFORMATION: Xaa = Asp, Glu, Gln or Asn
<220> FEATURE:
<221> NAME/KEY: MOD_RES
<222> LOCATION: (4)..(4)
<223> OTHER INFORMATION: Xaa = Val or Leu

<400> SEQUENCE: 38

Xaa Xaa Xaa Xaa
1

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide

<400> SEQUENCE: 39

Glu Thr Asp Val
1

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Glu Thr Glu Val
1
```

```
<210> SEQ ID NO 41
<211> LENGTH: 4
<212> TYPE: PRT
<213> ORGANISM: Artificial Sequence
<220> FEATURE:
<223> OTHER INFORMATION: Synthetic peptide

<400> SEQUENCE: 41

Asp Thr Asp Val
1

<210> SEQ ID NO 42
<211> LENGTH: 4
<212> TYPE: PRT
<213> ORGANISM: Artificial Sequence
<220> FEATURE:
<223> OTHER INFORMATION: Synthetic peptide

<400> SEQUENCE: 42

Asp Thr Glu Val
1

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Lys Leu Ser Ser Ile Glu Thr Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Thr Gly Glu Lys Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide

<400> SEQUENCE: 46

Gly Gly Arg Arg Gly Gly Gly Ser
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Leu Arg Gln Arg Asp Gly Glu Arg Pro
1               5

<210> SEQ ID NO 48
<211> LENGTH: 13
<212> TYPE: PRT
<213> ORGANISM: Artificial Sequence
<220> FEATURE:
<223> OTHER INFORMATION: Synthetic peptide

<400> SEQUENCE: 48

Tyr Gly Arg Lys Lys Arg Arg Gln Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic variant of tat peptide
<220> FEATURE:
<221> NAME/KEY: MOD_RES
<222> LOCATION: (1)..(1)
<223> OTHER INFORMATION: Xaa is any amino acid other than Tyr or absent

<400> SEQUENCE: 49

Xaa Gly Arg Lys Lys Arg Arg Gln Arg Arg
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 50

Gly Lys Lys Lys Lys Lys Gln Lys Lys Lys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 51

Arg Lys Lys Arg Arg Gln Arg Arg Arg
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 52

Gly Ala Lys Lys Arg Arg Gln Arg Arg Arg
```

<210> SEQ ID NO 53
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 53

Ala Lys Lys Arg Arg Gln Arg Arg Arg
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 54

Gly Arg Lys Ala Arg Arg Gln Arg Arg Arg
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 55

Arg Lys Ala Arg Arg Gln Arg Arg Arg
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 56

Gly Arg Lys Lys Ala Arg Gln Arg Arg Arg
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 57

Arg Lys Lys Ala Arg Gln Arg Arg Arg
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 58

Gly Arg Lys Lys Arg Arg Gln Ala Arg Arg
1               5                   10

```
<210> SEQ ID NO 59
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 59

Arg Lys Lys Arg Arg Gln Ala Arg Arg
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 60

Gly Arg Lys Lys Arg Arg Gln Arg Ala Arg
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic tat peptide

<400> SEQUENCE: 61

Arg Lys Lys Arg Arg Gln Arg Ala Arg
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 62

Arg Arg Pro Arg Arg Pro Arg Arg Pro Arg Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 63

Arg Arg Ala Arg Arg Ala Arg Arg Ala Arg Arg
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 64

Arg Arg Arg Ala Arg Arg Arg Ala Arg Arg
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Synthetic tat peptide

<400> SEQUENCE: 65

Arg Arg Arg Pro Arg Arg Arg Pro Arg Arg
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Synthetic tat peptide

<400> SEQUENCE: 66

Arg Arg Pro Arg Arg Pro Arg Arg
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic tat peptide

<400> SEQUENCE: 67

Arg Arg Ala Arg Arg Ala Arg Arg
1               5

<210> SEQ ID NO 68
<211> LENGTH: 4
<212> TYPE: PRT
<213> ORGANISM: Artificial Sequence
<220> FEATURE:
<223> OTHER INFORMATION: synthetic peptide analog of NR2B9c
<220> FEATURE:
<221> NAME/KEY: MOD_RES
<222> LOCATION: (1)...(1)
<223> OTHER INFORMATION: Xaa = Glu, Gln, and Ala, or an analogue thereof
<220> FEATURE:
<221> NAME/KEY: MOD_RES
<222> LOCATION: (2)...(2)
<223> OTHER INFORMATION: Xaa = Thr or Ser
<220> FEATURE:
<221> NAME/KEY: MOD_RES
<222> LOCATION: (3)...(3)
<223> OTHER INFORMATION: Xaa = Ala, Gln, Asp, Asn, N-Me-Ala, N-Me-Gln,
      N-Me-Asp,and N-Me-Asn or an analogue thereof

<400> SEQUENCE: 68

Xaa Xaa Xaa Val
1

<210> SEQ ID NO 69
<211> LENGTH: 22
<212> TYPE: PRT
<213> ORGANISM: Artificial Sequence
<220> FEATURE:
<223> OTHER INFORMATION: synthetic retro-inverso analog of Tat-NR2B9c

<400> SEQUENCE: 69

Val Asp Ser Glu Ile Ser Ser Leu Lys Arg Arg Arg Gln Arg Arg Lys
1               5                   10                  15

Lys Arg Gly Tyr Ile Asn
```

```
<210> SEQ ID NO 70
<211> LENGTH: 20
<212> TYPE: PRT
<213> ORGANISM: Artificial Sequence
<220> FEATURE:
<223> OTHER INFORMATION: synthetic peptide RvTat-NR2B9c

<400> SEQUENCE: 70

Arg Arg Arg Gln Arg Arg Lys Lys Arg Gly Tyr Lys Leu Ser Ser Ile
1               5                   10                  15

Glu Ser Asp Val
            20

<210> SEQ ID NO 71
<211> LENGTH: 5
<212> TYPE: PRT
<213> ORGANISM: Artificial Sequence
<220> FEATURE:
<223> OTHER INFORMATION: synthetic pentamer peptide from the C-terminus
      of NMDAR 2B

<400> SEQUENCE: 71

Ile Glu Ser Asp Val
1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic tat peptide

<400> SEQUENCE: 72

Gly Arg Lys Lys Arg Arg Gln Arg Arg Arg Pro
1               5                   10
```